United States Patent
Wang et al.

(10) Patent No.: US 10,746,738 B2
(45) Date of Patent: Aug. 18, 2020

(54) CLAUDIN-1 PEPTIDE REAGENTS AND METHODS

(71) Applicant: THE REGENTS OF THE UNIVERSITY OF MICHIGAN, Ann Arbor, MI (US)

(72) Inventors: Thomas D. Wang, Ann Arbor, MI (US); Emily Rabinsky, Ann Arbor, MI (US); Bishnu P. Joshi, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/553,645

(22) PCT Filed: Feb. 25, 2016

(86) PCT No.: PCT/US2016/019528
§ 371 (c)(1),
(2) Date: Aug. 25, 2017

(87) PCT Pub. No.: WO2016/138245
PCT Pub. Date: Sep. 1, 2016

(65) Prior Publication Data
US 2018/0052165 A1 Feb. 22, 2018

Related U.S. Application Data

(60) Provisional application No. 62/121,663, filed on Feb. 27, 2015.

(51) Int. Cl.
| G01N 33/574 | (2006.01) |
| A61K 49/00 | (2006.01) |
| C07K 7/06 | (2006.01) |
| C07K 16/30 | (2006.01) |

(52) U.S. Cl.
CPC ... *G01N 33/57419* (2013.01); *A61K 49/0032* (2013.01); *A61K 49/0056* (2013.01); *C07K 7/06* (2013.01); *C07K 16/30* (2013.01)

(58) Field of Classification Search
None
See application file for complete search history.

(56) References Cited

U.S. PATENT DOCUMENTS

| 2008/0227098 A1 | 9/2008 | Krajewska et al. | |
| 2009/0305900 A1* | 12/2009 | Belouchi | C12Q 1/6883 506/7 |
| 2011/0104263 A1 | 5/2011 | Lo et al. | |
| 2011/0236347 A1* | 9/2011 | Baumert | C07K 16/28 424/85.4 |
| 2014/0105827 A1 | 4/2014 | Morse et al. | |

FOREIGN PATENT DOCUMENTS

| WO | WO-2002/014499 A2 | 2/2002 |
| WO | WO-2003/033515 A1 | 4/2003 |
| WO | WO-2003/069307 A2 | 8/2003 |
| WO | WO-2012/083338 A1 | 6/2012 |
| WO | WO-2012/135824 A2 | 10/2012 |

OTHER PUBLICATIONS

Kelly et al (Cancer Res 64:6247-6251, 2004, IDS item #C10, filed on Dec. 19, 2017 (Year: 2004).*
Cwirla et al., Peptides on phage: a vast library of peptides for identifying ligands. *Proc. Natl. Acad. Sci. USA*, 87: 6378-82 (1990).
de Oliveira et al., Claudins upregulation in human colorectal cancer. *FEBS Lett.* 579: 6179-85 (2005).
Dhawan et al., Claudin-1 regulates cellular transformation and metastatic behavior in colon cancer. *J. Clin. Invest.* 115: 1765-76 (2005).
Essler et al., Molecular specialization of breast vasculature: a breast-homing phage-displayed peptide binds to aminopeptidase P in breast vasculature. *Proc. Natl. Acad. Sci. USA*, 99: 2252-7 (2002).
Fluge et al., Gene expression in poorly differentiated papillary thyroid carcinomas. *Thyroid*, 16: 161-75 (2006).
Gröne et al., Differential expression of genes encoding tight junction proteins in colorectal cancer: frequent dysregulation of claudin-1, -8 and -12. *Int. J. Colorectal Dis.* 22: 651-9 (2007).
Hsiung et al., Detection of colonic dysplasia in vivo using a targeted heptapeptide and confocal microendoscopy. *Nat. Med.* 14: 454-8 (2008).
Iacobuzio-Donahue et al., Discovery of novel tumor markers of pancreatic cancer using global gene expression technology. *Am. J. Pathol.* 160: 1239-49 (2002).
Joyce et al., Stage-specific vascular markers revealed by phage display in a mouse model of pancreatic islet tumorigenesis. *Cancer Cell*, 4: 393-403 (2003).
Kelly et al., Detection of invasive colon cancer using a novel, targeted, library-derived fluorescent peptide. *Cancer Res.* 64: 6247-51 (2004).
Kinugasa et al., Selective up-regulation of claudin-1 and claudin-2 in colorectal cancer. *Anticancer Res.* 27(6A): 3729-34 (2007).
Kinugasa et al., Increased claudin-1 protein expression contributes to tumorigenesis in ulcerative colitis-associated colorectal cancer. *Anticancer Res.* 30: 3181-6 (2010).
Lee et al., Increased expressions of claudin-1 and claudin-7 during the progression of cervical neoplasia. *Gynecol. Oncol.* 97: 53-9 (2005).
Lee et al., Targeting bladder tumor cells in vivo and in the urine with a peptide identified by phage display. *Mol. Cancer Res.* 5(1): 11-9 (2007).
Li et al., Affinity peptide for targeted detection of dysplasia in Barrett's esophagus. *Gastroenterology*, 139:1472-80 (2010).

(Continued)

*Primary Examiner* — Lei Yao
(74) *Attorney, Agent, or Firm* — Marshall, Gerstein & Borun LLP

(57) ABSTRACT

The present invention is directed to claudin-1-specific peptide reagents, methods for detecting pre-cancer (dysplasia), early cancer and/or cancer using the peptide reagents, and methods for targeting pre-cancerous (dysplastic) cells, and/or cancer cells using the peptide reagents.

10 Claims, 12 Drawing Sheets

Specification includes a Sequence Listing.

(56) References Cited

OTHER PUBLICATIONS

Ludtke et al., In vivo selection and validation of liver-specific ligands using a new T7 phage peptide display system. *Drug Deliv.* 14: 357-69 (2007).
Mees et al., Expression of tight and adherens junction proteins in ulcerative colitis associated colorectal carcinoma: upregulation of claudin-1, claudin-3, claudin-4, and beta-catenin. *Int. J. Colorectal Dis.* 24: 361-8 (2009).
Miwa et al., Involvement of claudin-1 in the beta-catenin/Tcf signaling pathway and its frequent upregulation in human colorectal cancers. *Oncol. Res.* 12: 469-76 (2001).
Morita et al., Tight junction-associated proteins (occludin, ZO-1, claudin-1, claudin-4) in squamous cell carcinoma and Bowen's disease. *Br. J. Dermatol.* 151: 328-34 (2004).
Mrsny et al., A key claudin extracellular loop domain is critical for epithelial barrier integrity. *Am. J. Pathol.* 172: 905-15 (2008).
Pasqualini et al., Organ targeting in vivo using phage display peptide libraries. *Nature,* 380: 364-6 (1996).
Resnick et al., Claudin expression in gastric adenocarcinomas: a tissue microarray study with prognostic correlation. *Hum. Pathol.* 36: 886-92 (2005).
Scott et al., Searching for peptide ligands with an epitope library. *Science,* 249: 386-90 (1990).
Sheffer et al., Association of survival and disease progression with chromosomal instability: a genomic exploration of colorectal cancer. *Proc. Natl. Acad. Sci USA,* 106: 7131-6 (2009).
Vogelstein et al., Cancer genome landscapes. *Science,* 339: 1546-58 (2013).
Weber et al., Claudin-1 and claudin-2 expression is elevated in inflammatory bowel disease and may contribute to early neoplastic transformation. *Lab. Invest.* 88: 1110-20 (2008).

* cited by examiner

SEQUENCE LISTING

```
<160> NUMBER OF SEQ ID NOS: 24

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Arg Thr Ser Pro Ser Ser Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

His Leu Gln Leu Gln Arg Leu
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Ile Gln Thr Asn Pro Thr Met
1               5
```

```
<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Arg Ser Leu Thr Gln Gln Thr
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Ser Leu Gln His Leu Arg Ser
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Ile Gln Leu Lys Ile Asn Ser
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Ile Thr Ile Arg Gln His Ile
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

Arg Arg Ser Asn Ser Gln Leu
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Leu Asn Arg Ile Arg Arg Arg
1               5
```

```
<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

Asn Asn Met Lys Lys Ile Thr
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Leu Gln Ser Leu Ile Ser Lys
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Ile His Thr Arg Arg Arg Lys
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Arg Pro Asn Lys Pro Arg Ile
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Arg His Arg Arg Ser Pro Ile
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Ile Thr Leu Ser Ile Thr Gln
1               5

<210> SEQ ID NO 16
```

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

Lys Thr Gln Leu Met Ile Ile
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Arg Pro Arg Gln Leu Gln Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Thr Arg Arg His Thr Ile Ile
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

Arg Ile Ile His Lys Asn Met
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide

<400> SEQUENCE: 20

Leu Leu Thr Ile Ser Pro Lys
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide

<400> SEQUENCE: 21

Leu Leu Pro Met His Met Asn
1               5

<210> SEQ ID NO 22
<211> LENGTH: 7
```

```
<212> TYPE: PRT
<213> ORGANISM: Artificial Sequence
<220> FEATURE:
<223> OTHER INFORMATION: Synthetic peptide

<400> SEQUENCE: 22

Thr Ser Pro Met Leu Ser Ile
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide

<400> SEQUENCE: 23

Leu Arg Asn Asn Ile Arg His
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic peptide

<400> SEQUENCE: 24

Gly Gly Gly Ser Lys
1               5
```

CLAUDIN-1 PEPTIDE REAGENTS AND METHODS

CROSS-REFERENCE TO RELATED APPLICATIONS

This application claims the benefit of U.S. Provisional Patent Application Ser. No. 62/121,663, filed Feb. 27, 2015, which is incorporated herein by reference in its entirety.

STATEMENT OF GOVERNMENT INTEREST

This invention was made with government support under CA163059 awarded by the National Institutes of Health. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 4,353 byte ACII (Text) file named "48981_SeqListing.txt," created on Dec. 23, 2014.

FIELD OF THE INVENTION

The present invention is directed to claudin-1-specific peptide reagents, methods for detecting pre-cancer, early cancer, and cancer using the peptide reagents, and methods for targeting precancerous cells, early cancer cells and cancerous cells using the peptide reagents.

BACKGROUND

Colorectal cancer (CRC) is one of the most common causes of cancer-related deaths in the world. Approximately 1,360,000 new cases were diagnosed globally in 2012, resulting in ~693,000 annual deaths. These numbers are expected to nearly double over the next 20 years with a rapid rise in obesity and more developing countries adopting a Western diet. Greater focus on early detection of pre-malignant lesions (dysplasia) is needed [Vogelstein et al., *Science*, 339: 1546-1558 (2013)].

Endoscopy is a frequently performed imaging exam that is widely accepted by patients and referring physicians. However, a significant miss rate of >25% has been found on back-to-back exams for grossly visible adenomatous polyps. Moreover, flat lesions can give rise to carcinoma, and has been found to be as high as 36% of all adenomas. Flat lesions have been found to be more aggressive than polyps, and five times more likely to harbor either in situ or submucosal carcinoma in some patient populations. Studies of outcomes also show that colonoscopy results in a minimal reduction in mortality for cancers that arise in the proximal colon (right side). Furthermore, cancer diagnosed after a "negative" colonoscopy occurs more frequently in the proximal colon. These findings have been attributed to greater genetic instability and a flat morphology. Thus, imaging methods that are sensitive to flat lesions may improve detection and prevention of CRC. Although colonoscopy is widely performed for screening, there is minimal reduction in mortality for carcinomas that arise in the proximal colon. Furthermore, cancer diagnosed after a "negative" colonoscopy occurs more frequently in the proximal colon. These findings have been attributed to greater microsatellite instability and a flat morphology.

Endoscopic imaging with use of exogenous fluorescent-labeled probes, is a promising method for achieving greater specificity in the detection of neoplastic lesions by identifying the expression of unique molecular targets. Imaging provides precise localization, and fluorescence provides improved contrast. Previously, several diagnostic molecules have been used as targeted agents, including antibodies and antibody fragments, for the detection of pre-malignant and malignant lesions in various types of cancer. However, the use of antibodies and antibody fragments is limited by immunogenicity, cost of production and long plasma half-life. Small molecules, RNA aptamers, and activatable probes have also been used. Peptides represent a new class of imaging agent that is compatible with clinical use in the digestive tract, in particular with topical administration.

Phage display is a powerful combinatorial technique for peptide discovery that uses methods of recombinant DNA technology to generate a complex library of peptides, often expressing up to 107-109 unique sequences, that can bind to cell surface antigens. The DNA of candidate phages can be recovered and sequenced, elucidating positive binding peptides that can then be synthetically fabricated. Phage display identified peptide binders to high grade dysplasia in Barrett's esophagus [Li et al., *Gastroenterology*, 139:1472-80 (2010)] and human colonic dysplasia [Hsiung et al., *Nat. Med.*, 14: 454-458 (2008)] using the commercially available NEB M13 phage system. The T7 system has proven effective in in vivo panning experiments identifying peptides specific to pancreatic islet vasculature [Joyce et al., *Cancer Cell*, 4: 393-403 (2003)], breast vasculature [Essler and Ruoslahti, *Proc. Natl. Acad. Sci. USA*, 99: 2252-2257 (2002)], bladder tumor cells [Lee et al., *Mol. Cancer Res.*, 5(1): 11-19 (2007)], and liver tissue [Ludtke et al., *Drug Deliv.*, 14: 357-369 (2007)]. Panning with intact tissue presents additional relevant cell targets while accounting for subtle features in the tissue microenvironment that may affect binding.

Claudin-1 (sometimes abbreviated CLDN1 herein) is an integral membrane protein that forms tight junctions between epithelial cells to regulate paracellular transport [Mrsny et al., *Am. J. Pathol.*, 172: 905-915 (2008)]. This protein is overexpressed in several human cancers, including colorectal [Dhawan et al., *J. Clin. Invest.*, 115:1765-1776 (2005); Miwa et al., *Oncol. Res.*, 12: 469-476 (2001); d Oliveira et al., *FEBS Lett.*, 579: 6179-6185 (2005)], pancreas [Iacobuzio-Donahue et al., *Am. J. Pathol.*, 160: 1239-1249 (2002)], cervical [Lee et al., *Gynecol. Oncol.*, 97: 53-59 (2005)], squamous cell [Morita et al., *Br. J. Dermatol.*, 151: 328-334 (2004)], stomach [Resnick et al., *Hum. Pathol.*, 36: 886-892 (2005)], and thyroid [Fluge et al., *Thyroid*, 16: 161-175 (2006)]. In colon, claudin-1 is found at levels >40-fold higher in neoplastic by comparison to normal mucosa [Kinugasa et al., *Anticancer Res.*, 27(6A): 3729-3734 (2007)]. These results have been found on gene and protein expression profile analyses [Sheffer et al., *Proc. Natl. Acad. Sci. USA*, 106: 7131-7136 (2009)], and have been validated on immunohistochemistry [Dhawan et al., *J. Clin. Invest.*, 115: 1765-1776 (2005)]. Overexpression of this protein in neoplasia is believed to increase cell proliferation, motility, and invasiveness, and may contribute to loss of cell polarity, abnormal cellular organization, and decreased differentiation [Gröne et al., *Int. J. Colorectal Dis.*, 22: 651-659 (2007)]. Claudin-1 has also been found to have increased expression in neoplasia associated with inflammatory bowel disease [Mees et al., *Int. J. Colorectal*

Dis., 24: 361-368 (2009); Weber et al., *Lab. Invest.*, 88: 1110-1120 (2008); Kinugasa et al., *Anticancer Res.*, 30: 3181-3186 (2010)].

Various methods for screening for or diagnosing cancer involving claudin-1 are mentioned in WO 2012/135824, WO 2003/069307, US 20080227098, WO 2002/014499 and WO 2012/083338.

New products and methods for early detection of precancer (dysplasia), early cancer and cancer are needed in the art. New products and methods for early detection would have important clinical applications for increasing the survival rate for CRC and other epithelial cell-derived cancers, and for reducing the healthcare costs.

SUMMARY

In one aspect, the disclosure provides a reagent consisting essentially of a peptide RTSPSSR (SEQ ID NO: 1), HLQLQRL (SEQ ID NO: 2), IQTNPTM (SEQ ID NO: 3), RSLTQQT (SEQ ID NO: 4), SLQHLRS (SEQ ID NO: 5), IQLKINS (SEQ ID NO: 6), ITIRQHI (SEQ ID NO: 7), RRSNSQL (SEQ ID NO: 8), LNRIRRR (SEQ ID NO: 9), NNMKKIT (SEQ ID NO: 10), LQSLISK (SEQ ID NO: 11), IHTRRRK (SEQ ID NO: 12), RPNKPRI (SEQ ID NO: 13), RHRRSPI (SEQ ID NO: 14), ITLSITQ (SEQ ID NO: 15), KTQLMII (SEQ ID NO: 16), RPRQLQR (SEQ ID NO: 17), TRRHTII (SEQ ID NO: 18), RIIHKNM (SEQ ID NO: 19), LLTISPK (SEQ ID NO: 20), LLPMHMN (SEQ ID NO: 21), TSPMLSI (SEQ ID NO: 22), or LRNNIRH SEQ ID NO: 23), or a multimer form of the peptide, wherein the reagents specifically bind to claudin-1. In some embodiments, the multimer form is a dimer.

In some embodiments, the reagent comprises at least one detectable label attached to the peptide or multimer form of the peptide. In some embodiments, the detectable label is detectable by microscopy, photoacoustic, ultrasound or magnetic resonance imaging. In some embodiments, the label detectable by microscopy is fluorescein isothiocyanate (FITC), Cy5, Cy5.5, or IRdye800. In some embodiments, the detectable label is attached to the peptide by a peptide linker. In some embodiments, the terminal amino acid of the linker is lysine. In some embodiment, the linker comprises the sequence GGGSK set out in SEQ ID NO: 24.

In some embodiments, the reagent comprises at least one therapeutic moiety attached to the peptide or multimer form of the peptide. In some embodiments, the therapeutic moiety is chemotherapeutic agent.

In some embodiments, the regent comprises at least one detectable label attached to the peptide or multimer form of the peptide and at least one therapeutic moiety attached to the peptide or multimer form of the peptide.

In another aspect, the disclosure provides a composition comprising a reagent of the invention and a pharmaceutically acceptable excipient.

In yet another aspect, the disclosure provides methods for detecting colon dysplasia in a patient comprising the steps of administering a reagent of the invention to the colon of the patient and detecting binding of the reagent to dysplastic cells.

In still another aspect, the disclosure provides methods for detecting dysplasia, early cancer or cancer in a patient comprising the steps of administering a reagent of the invention to the patient and detecting binding of the reagent. In another aspect, the disclosure provides a method of determining the effectiveness of a treatment for cancer and/or cancer metastasis, or recurrence of cancer in a patient comprising the step of administering a reagent of the invention to the patient, visualizing a first amount of cells labeled with the reagent, and comparing the first amount to a previously-visualized second amount of cells labeled with the reagent, wherein a decrease in the first amount cells labeled relative to the previously-visualized second amount of cells labeled is indicative of effective treatment. In some embodiments, the methods further comprise obtaining a biopsy of the cells labeled by the reagent.

In yet another aspect, the disclosure provides a method for delivering a therapeutic moiety to dysplastic cells of a patient comprising the step of administering a reagent of the invention to the patient.

In still another aspect, the disclosure provides a method for delivering a therapeutic moiety to early cancer cells of a patient comprising the step of administering a reagent of the invention to the patient.

In still another aspect, the disclosure provides a method for delivering a therapeutic moiety to cancer cells of a patient comprising the step of administering a reagent of the invention to the patient.

In the methods of each aspect described herein, dysplasia, early cancer or cancer arising from epithelial cells in, for example, colon, cervix, squamous cell, thyroid, brain, breast, prostate, liver, lung esophagus, stomach, bladder, biliary tract, pancreas and skin is specifically contemplated.

In a further aspect, the disclosure provides a kit for administering a composition of the invention to a patient in need thereof, comprising the composition, instructions for use of the composition and a device for administering the composition to the patient.

In another aspect, the disclosure provides a peptide consisting of the amino acid sequence RTSPSSR (SEQ ID NO: 1), HLQLQRL (SEQ ID NO: 2), IQTNPTM (SEQ ID NO: 3), RSLTQQT (SEQ ID NO: 4), SLQHLRS (SEQ ID NO: 5), IQLKINS (SEQ ID NO: 6), ITIRQHI (SEQ ID NO: 7), RRSNSQL (SEQ ID NO: 8), LNRIRRR (SEQ ID NO: 9), NNMKKIT (SEQ ID NO: 10), LQSLISK (SEQ ID NO: 11), IHTRRRK (SEQ ID NO: 12), RPNKPRI (SEQ ID NO: 13), RHRRSPI (SEQ ID NO: 14), ITLSITQ (SEQ ID NO: 15), KTQLMII (SEQ ID NO: 16), RPRQLQR (SEQ ID NO: 17), TRRHTII (SEQ ID NO: 18), RIIHKNM (SEQ ID NO: 19), LLTISPK (SEQ ID NO: 20), LLPMHMN (SEQ ID NO: 21), TSPMLSI (SEQ ID NO: 22), or LRNNIRH SEQ ID NO: 23).

DESCRIPTION

Figure 1:
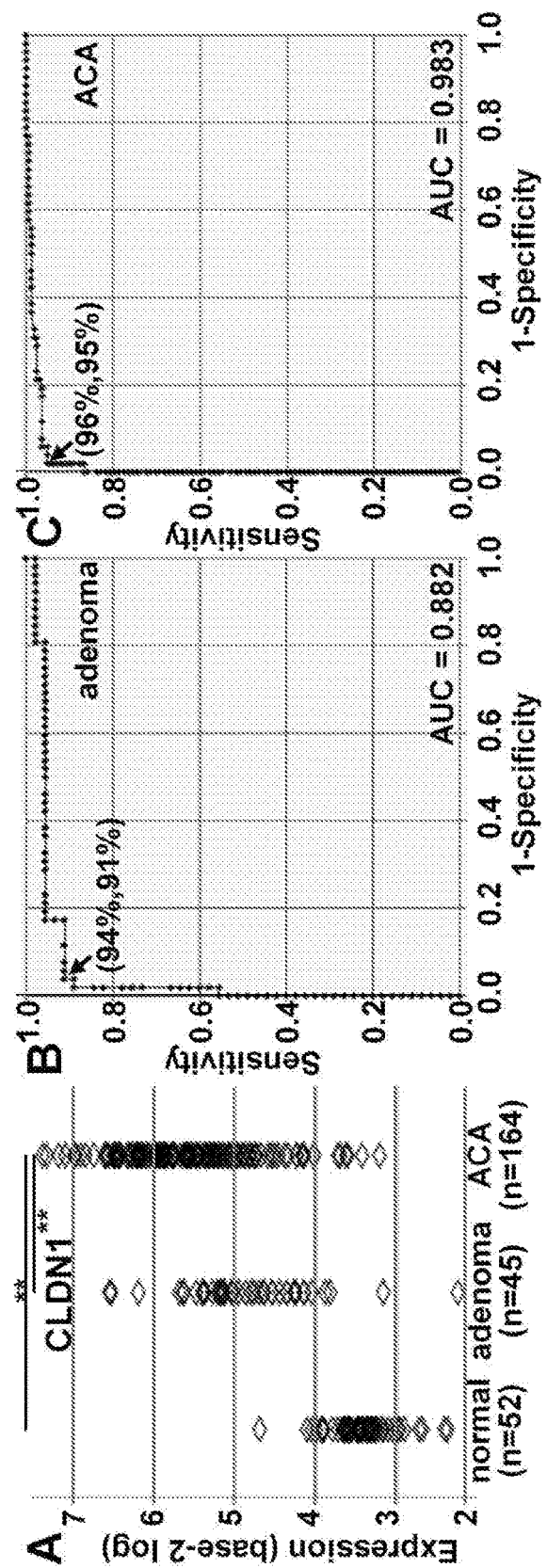
FIG. 1 shows the results of an analysis of gene expression data that reveals claudin-1 overexpression in colonic neoplasia. A) Distribution of claudin-1 gene expression level in normal colon (n=52), adenoma (n=45), and adenocarcinoma (ACA, n=164), **P-value <0.05. B,C) ROC curves for adenoma and ACA shows potential for high detection sensitivity and specificity with AUC of 0.882 and 0.983, respectively.

Transformed cells and tissues express molecular changes well in advance of gross morphological changes, thus providing a unique opportunity for the early detection of cancer. Peptides that bind to pre-cancerous lesions have the potential to guide tissue biopsy for lesions that are endoscopically "invisible." Peptides have in vivo advantages because they can be delivered topically to identify early molecular changes on the surface of epithelial cells where cancer originates. In addition, they can exhibit rapid binding kinetics and also diffuse into diseased tissue.

In one aspect, the invention provides peptides that bind to claudin-1 expressed on dysplastic cells and/or cancerous cells. The peptides include, but are not limited to, the peptides RTSPSSR (SEQ ID NO: 1), HLQLQRL (SEQ ID NO: 2), IQTNPTM (SEQ ID NO: 3), RSLTQQT (SEQ ID NO: 4), SLQHLRS (SEQ ID NO: 5), IQLKINS (SEQ ID NO: 6), ITIRQHI (SEQ ID NO: 7), RRSNSQL (SEQ ID NO: 8), LNRIRRR (SEQ ID NO: 9), NNMKKIT (SEQ ID NO: 10), LQSLISK (SEQ ID NO: 11), IHTRRRK (SEQ ID NO: 12), RPNKPRI (SEQ ID NO: 13), RHRRSPI (SEQ ID NO: 14), ITLSITQ (SEQ ID NO: 15), KTQLMII (SEQ ID NO: 16), RPRQLQR (SEQ ID NO: 17), TRRHTII (SEQ ID NO: 18), RIIHKNM (SEQ ID NO: 19), LLTISPK (SEQ ID NO: 20), LLPMHMN (SEQ ID NO: 21), TSPMLSI (SEQ ID NO: 22), or LRNNIRH SEQ ID NO: 23).

In a further aspect, the invention provides reagents comprising a peptide of the invention. A "reagent" of the invention comprises at least two components, a peptide of the invention and another moiety attached to the peptide. The only component of the reagent that contributes to binding of claudin-1 is the peptide of the invention. In other words, the reagent "consists essentially of" a peptide of the invention. In some embodiments, the other moiety comprises amino acids but the peptide of the invention is not linked to those amino acids in nature and the other amino acids do not affect binding of the peptide to claudin-1. Moreover, the other moiety in a reagent contemplated herein is not a phage in a phage display library or a component of any other type of peptide display library.

In some embodiments, the reagents comprise at least one detectable label as a moiety attached to a peptide of the invention. The detectable label may be detectable, for example, by microscopy, ultrasound, PET, SPECT, or magnetic resonance imaging. In some embodiments the label detectable by microscopy is fluorescein isothiocyanate (FITC), Cy5, Cy5.5 and IRdye800.

In some embodiments, the detectable label is attached to a peptide of the invention by a peptide linker. The terminal amino acid of the linker by be a lysine such as in the exemplary linker GGGSK (SEQ ID NO: 24).

In some embodiments, the reagents comprise at least one therapeutic moiety attached to a peptide of the invention. The therapeutic moiety may be a chemopreventative or chemotherapeutic agent. In certain embodiments, the therapeutic moiety is celecoxib, 5-fluorouracil, and/or chlorambucil.

In some embodiments, the regent comprises at least one detectable label attached to the peptide or multimer form of the peptide, and at least one therapeutic moiety attached to the peptide or multimer form of the peptide.

In yet a further aspect, the invention provides a composition comprising a reagent of the invention and a pharmaceutically acceptable excipient.

In still a further aspect, the invention provides a method for specifically detecting pre-cancer (dysplasia), early cancer and/or cancer in a patient comprising the steps of administering a reagent of the invention attached to a detectable label to the patient and detecting binding of the reagent to dysplastic cells or early cancer cells. In some embodiments, the detectable binding takes place in vivo. In others, the detectable binding takes places in vitro. In still others, the detectable binding takes place in situ. Detection of pre-cancer (dysplasia), early cancer and/or cancer arising from epithelial cells is specifically contemplated. Dysplasia, early cancer or cancer arising from epithelial cells in, for example, colon, cervix, squamous cell, thyroid, brain, breast, prostate, liver, lung esophagus, stomach, bladder, biliary tract, pancreas and skin is specifically contemplated.

The phrase "specifically detects" means that the reagent binds to and is detected in association with a type of cell, and the reagent does not bind to and is not detected in association with another type of cell at the level of sensitivity at which the method is carried out.

In the colon, the transformation from pre-malignant mucosa to carcinoma involves the development of flat and depressed (non-polypoid) lesions, adenomatous polyps (polypoid lesions) and then frank carcinoma (colon cancer cells). Detecting colon dysplasia (i.e., dysplastic cells), pre-cancerous cells and/or cancerous according to the invention includes detecting binding to flat and depressed lesions, adenomatous polyps and/or cancer cells. In some embodiments, a reagent of the invention specifically detects cells of flat and depressed lesions. In some embodiments, a reagent of the invention specifically detects cells of adenomatous polyps. In some embodiments, a reagent of the invention specifically detects colon cancer cells. In some embodiments, a reagent of the invention may specifically detect two or more of cells of flat and depressed lesions, cells of adenomatous polyps and colon cancer cells.

Flat dysplastic lesions are also observed in the setting of chronic ulcerative colitis and are also contemplated to be detectable by methods of the invention.

In an additional aspect, the invention provides a method of determining the effectiveness of a treatment for cancer and/or cancer metastasis, or recurrence of cancer in a patient comprising the step of administering a reagent of the invention attached to a detectable label to the patient, visualizing a first amount of cells labeled with the reagent, and comparing the first amount to a previously-visualized second amount of cells labeled with the reagent, wherein a decrease in the first amount cells labeled relative to the previously-visualized second amount of cells labeled is indicative of effective treatment. In some embodiments, a decrease of 5% is indicative of effective treatment. In other embodiments, a decrease of about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or more is indicative of effective treatment. In some embodiments, the method further comprises obtaining a biopsy of the cells labeled by the reagent.

In another aspect, the invention provides a method for delivering a therapeutic moiety to a patient comprising the step of administering a reagent of the invention attached to a therapeutic moiety to the patient.

In yet another aspect, the invention provides a method for delivering a therapeutic moiety to colon cancer cells of a patient comprising the step of administering a reagent of the invention attached to a therapeutic moiety to the colon of the patient.

In still another aspect, the invention provides a kit for administering a composition of the invention to a patient in need thereof, where the kit comprises a composition of invention, instructions for use of the composition and a device for administering the composition to the patient.

Linkers, Peptides and Peptide Analogs

As used herein, a "linker" is a sequence of amino acids located at the C-terminus of a peptide of the disclosure. In some embodiments, the linker sequence terminates with a lysine residue.

In some embodiments, the presence of a linker results in at least a 1% increase in detectable binding of a reagent of the invention to dysplastic colon cells or cancerous colon cells compared to the detectable binding of the reagent in the absence of the linker. In various aspects, the increase in detectable binding is at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, at least about 50-fold, at least about 100-fold or more.

The term "peptide" refers to molecules of 2 to 50 amino acids, molecules of 3 to 20 amino acids, and those of 6 to 15 amino acids. Peptides and linkers as contemplated by the invention may be 5 amino acids in length. In various aspects, a polypeptide or linker may be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids in length.

Exemplary peptides are, in various aspects, randomly generated by methods known in the art, carried in a polypeptide library (for example and without limitation, a phage display library), derived by digestion of proteins, or chemically synthesized. Peptides exemplified in the present disclosure have been developed using techniques of phage display, a powerful combinatorial method that uses recombinant DNA technology to generate a complex library of polypeptides for selection by preferential binding to cell surface targets [Scott et al., *Science*, 249:386-390 (1990)]. The protein coat of bacteriophage, such as the filamentous M13 or icosahedral T7, is genetically engineered to express a very large number (>$10^9$) of different polypeptides with unique sequences to achieve affinity binding [Cwirla et al., *Proc. Natl. Acad. Sci. USA*, 87:6378-6382 (1990)]. Selection is then performed by biopanning the phage library against cultured cells and tissues that over express the target. The DNA sequences of these candidate phage are then recovered and used to synthesize the polypeptide [Pasqualini et al., *Nature*, 380:364-366 (1996)]. The polypeptides that preferentially bind to dysplastic mucosa are optionally labeled with fluorescence dyes, including but not limited to, FITC, Cy 5.5, Cy 7, and Li-Cor. These polypeptide-dye reagents have been developed and have demonstrated preferential binding to colon cancer (HT29) cells in culture and to pre-clinical xenograft models [Kelly et al., *Cancer Res.*, 64:6247-51 (2004)].

Peptides include D and L forms, either purified or in a mixture of the two forms. Also contemplated by the present disclosure are peptides that compete with peptides of the invention for binding to colon cells.

In some embodiments, a peptide of a reagent of the invention is presented in multimer form. Various scaffolds are known in the art upon which multiple peptides can be presented. In some embodiments, a peptide is presented in multimer form on a trilysine dendritic wedge. In some embodiments, a peptide is presented in dimer form using an aminohexanoic acid linker. Other scaffolds known in the art include, but are not limited to, other dendrimers and polymeric (e.g., PEG) scaffolds.

It will be understood that peptides and linkers of the invention optionally incorporate modifications known in the art and that the location and number of such modifications are varied to achieve an optimal effect in the peptide and/or linker analog.

In some embodiments, the compound is a peptide analog having a structure based on one of the peptides disclosed herein (the "parent peptide") but differs from the parent peptide in one or more respects. Accordingly, as appreciated by one of ordinary skill in the art, the teachings regarding the parent peptides provided herein may also be applicable to the peptide analogs.

In some embodiments, the peptide analog comprises the structure of a parent peptide, except that the peptide analog comprises one or more non-peptide bonds in place of peptide bond(s). In some embodiments, the peptide analog comprises in place of a peptide bond, an ester bond, an ether bond, a thioether bond, an amide bond, and the like. In some embodiments, the peptide analog is a depsipeptide comprising an ester linkage in place of a peptide bond.

In some embodiments, the peptide analog comprises the structure of a parent peptide described herein, except that the peptide analog comprises one or more amino acid substitutions, e.g., one or more conservative amino acid substitutions. Conservative amino acid substitutions are known in the art, and include amino acid substitutions in which one amino acid having certain physical and/or chemical properties is exchanged for another amino acid that has the same chemical or physical properties. For instance, the conservative amino acid substitution may be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

In some aspects, the peptide analog comprises one or more synthetic amino acids, e.g., an amino acid non-native to a mammal. Synthetic amino acids include β-alanine (β-Ala), N-α-methyl-alanine (Me-Ala), aminobutyric acid (Abu), γ-aminobutyric acid (γ-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met(O$_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-NO$_2$)), 4-cyanophenylalanine ((Phe(4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,-tetrahydro-isoquinoline-3-carboxylic acid (Tic), tetrahydropyranglycine, thienylalanine (Thi), O-benzyl-phosphotyrosine, 0-Phosphotyrosine, methoxytyrosine, ethoxytyrosine, O-(bis-dimethylamino-phosphono)-tyrosine, tyrosine sulfate tetrabutylamine, methyl-valine (Me-Val), and alkylated 3-mercaptopropionic acid.

In some embodiments, the peptide analog comprises one or more non-conservative amino acid substitutions and the peptide analog still functions to a similar extent, the same extent, or an improved extent as the parent peptide. In certain embodiments, the peptide analog comprising one or more non-conservative amino acid substitutions exhibits about the same or greater binding to dysplastic cells or early cancer cells in comparison to the parent peptide.

In some embodiments, the peptide analog comprises one or more amino acid insertions or deletions, in comparison to the parent peptide described herein. In some embodiments, the peptide analog comprises an insertion of one or more amino acids in comparison to the parent peptide. In some embodiments, the peptide analog comprises a deletion of one or more amino acids in comparison to the parent peptide. In some embodiments, the peptide analog comprises an insertion of one or more amino acids at the N- or C-terminus in comparison to the parent peptide. In some embodiments, the peptide analog comprises a deletion of one or more amino acids at the N- or C-terminus in comparison to the parent peptide. In these embodiments, the peptide analog still exhibits about the same or greater binding to dysplastic cells or early cancer cells in comparison to the parent peptide.

Detectable Markers

As used herein, a "detectable marker" is any label that can be used to identify the binding of a composition of the disclosure to dysplastic cells or early cancer cells. Non-limiting examples of detectable markers are fluorophores, chemical or protein tags that enable the visualization of a polypeptide. Visualization in certain aspects is carried out with the naked eye, or a device (for example and without limitation, an endoscope) and may also involve an alternate light or energy source.

Fluorophores, chemical and protein tags that are contemplated for use in the invention include, but are not limited to, FITC, Cy 5.5, Cy 7, Li-Cor, a radiolabel, biotin, luciferase, 1,8-ANS (1-Anilinonaphthalene-8-sulfonic acid), 1-Anilinonaphthalene-8-sulfonic acid (1,8-ANS), 5- (and -6)-Carboxy-2',7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, C5.5, CyQUANT GR-DNA, Dansyl Cadaverine, Dansyl Cadaverine, MeOH, DAPI, DAPI-DNA, Dapoxyl (2-aminoethyl) sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, eYFP (Enhanced Yellow Fluorescent Protein), FDA, FITC antibody conjugate pH 8.0, FlAsH, Fluo-3, Fluo-3 Ca2+, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red Ca2+, Fura Red, high Ca, Fura Red, low Ca, Fura-2 Ca2+, Fura-2, Fura-2, GFP (S65T), HcRed, Indo-1 Ca2+, Indo-1, Ca free, Indo-1, Ca saturated, JC-1, JC-1 pH 8.2, Lissamine rhodamine, *Lucifer* Yellow, CH, Magnesium Green, Magnesium Green Mg2+, Magnesium Orange, Marina Blue, mBanana, mCherry, mHoneydew, mOrange, mPlum, mRFP, mStrawberry, mTangerine, NBD-X, NBD-X, MeOH, NeuroTrace 500/525, green fluorescent Nissl stain-RNA, Nile Blue, Nile Red, Nile Red-lipid, Nissl, Oreg. Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, R-Phycoerythrin pH 7.5, ReAsH, Resorufin, Resorufin pH 9.0, Rhod-2, Rhod-2 Ca2+, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodamine Green pH 7.0, Rhodol Green antibody conjugate pH 8.0, Sapphire, SBFI-Na+, Sodium Green Na+, Sulforhodamine 101, Tetramethylrhodamine antibody conjugate pH 8.0, Tetramethylrhodamine dextran pH 7.0, and Texas Red-X antibody conjugate pH 7.2.

Non-limiting examples of chemical tags contemplated by the invention include radiolabels. For example and without limitation, radiolabels that contemplated in the compositions and methods of the present disclosure include $^{11}$C, $^{13}$N, $^{15}$O, $^{18}$F, $^{32}$P, $^{52}$Fe, $^{62}$Cu, $^{64}$Cu, $^{67}$Cu, $^{67}$Ga, $^{68}$Ga, $^{86}$Y, $^{89}$Zr, $^{90}$Y, $^{94m}$Tc, $^{94}$Tc, $^{95}$Tc, $^{99m}$Tc, $^{103}$Pd, $^{105}$Rh, $^{109}$Pd, $^{111}$Ag, $^{111}$In, $^{123}$I, $^{124}$I, $^{125}$I, $^{131}$I, $^{140}$La, $^{149}$Pm, $^{153}$Sm, $^{154-159}$Gd, $^{165}$Dy, $^{166}$Dy, $^{166}$Ho, $^{169}$Yb, $^{175}$Yb, $^{175}$Lu, $^{177}$Lu, $^{186}$Re, $^{188}$Re, $^{192}$Ir, $^{198}$Au, $^{199}$Au, and $^{212}$Bi.

A worker of ordinary skill in the art will appreciate that there are many such detectable markers that can be used to visualize a cell, in vitro, in vivo or ex vivo.

Therapeutic Moieties

Therapeutic moieties contemplated by the invention include, but are not limited to polypeptides (including protein therapeutics) or peptides, small molecules, chemotherapeutic agents, or combinations thereof.

The term "small molecule", as used herein, refers to a chemical compound, for instance a peptidometic or oligonucleotide that may optionally be derivatized, or any other low molecular weight organic compound, either natural or synthetic.

By "low molecular weight" is meant compounds having a molecular weight of less than 1000 Daltons, typically between 300 and 700 Daltons. Low molecular weight compounds, in various aspects, are about 100, about 150, about 200, about 250, about 300, about 350, about 400, about 450, about 500, about 550, about 600, about 650, about 700, about 750, about 800, about 850, about 900, about 1000 or more Daltons.

In some embodiments, the therapeutic moiety is a protein therapeutic. Protein therapeutics include, without limitation, cellular or circulating proteins as well as fragments and derivatives thereof. Still other therapeutic moieties include polynucleotides, including without limitation, protein coding polynucleotides, polynucleotides encoding regulatory polynucleotides, and/or polynucleotides which are regulatory in themselves. Optionally, the compositions comprise a combination of the compounds described herein.

In some embodiments, protein therapeutics include cytokines or hematopoietic factors including without limitation IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IL-7, IL-8, IL-9, IL-10, IL-12, IL-13, IL-14, IL-15, IL-16, IL-17, IL-18, thrombopoietin (TPO), angiopoietins, for example Ang-1, Ang-2, Ang-4, Ang-Y, the human angiopoietin-like polypeptide, vascular endothelial growth factor (VEGF), angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor $2\alpha$, cytokine-induced neutrophil chemotactic factor $2\beta$, $\beta$ endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor $\alpha$1, glial cell line-derived neutrophic factor receptor $\alpha$2, growth related protein, growth related protein $\alpha$, growth related protein $\beta$, growth related protein $\gamma$, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor $\alpha$, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor $\alpha$, platelet derived growth factor receptor $\beta$, pre-B cell growth stimulating factor, stem cell factor receptor, TNF, including TNF0, TNF1, TNF2, transforming growth factor $\alpha$, transforming growth factor $\beta$, transforming growth factor $\beta$1, transforming growth factor $\beta$1.2, transforming growth factor $\beta$2, transforming growth factor $\beta$3, transforming growth factor $\beta$5, latent transforming growth factor $\beta$1, transforming growth factor $\beta$ binding protein I, transforming growth factor $\beta$ binding protein II, transforming growth factor $\beta$ binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

Therapeutic moieties also include, in some embodiments, chemotherapeutic agents. A chemotherapeutic agent contemplated for use in a reagent of the invention includes, without limitation, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinium coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide. Gefitinib and erlotinib are also specifically contemplated.

Dosages of the therapeutic moiety provided are administered as a dose measured in, for example, mg/kg. Contemplated mg/kg doses of the disclosed therapeutics include about 1 mg/kg to about 60 mg/kg. Specific ranges of doses in mg/kg include about 1 mg/kg to about 20 mg/kg, about 5 mg/kg to about 20 mg/kg, about 10 mg/kg to about 20 mg/kg, about 25 mg/kg to about 50 mg/kg, and about 30 mg/kg to about 60 mg/kg. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

"Effective amount" as used herein refers to an amount of a reagent of the invention sufficient to visualize the identified disease or condition, or to exhibit a detectable therapeutic or inhibitory effect. The effect is detected by, for example, an improvement in clinical condition or reduction in symptoms. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

Visualization of Reagents

Visualization of binding to dysplastic cells or early cancer cells is by any means known to those of ordinary skill in the art. As discussed herein, visualization is, for example and without limitation, in vivo, in vitro, or in situ visualization.

In some embodiments where the detectable label is a radiolabel, the radiolabel is detected by nuclear imaging. Nuclear imaging is understood in the art to be a method of producing images by detecting radiation from different parts of the body after a radioactive tracer material is administered. The images are recorded on computer and on film.

Some embodiments of methods of the invention involve the acquisition of a tissue sample from a patient. The tissue sample is selected from the group consisting of a tissue or organ of said patient.

Formulations

Compositions of the invention are formulated with pharmaceutically acceptable excipients such as carriers, solvents, stabilizers, adjuvants, diluents, etc., depending upon the particular mode of administration and dosage form. The compositions are generally formulated to achieve a physiologically compatible pH, and range from a pH of about 3 to a pH of about 11, about pH 3 to about pH 7, depending on the formulation and route of administration. In alternative embodiments, the pH is adjusted to a range from about pH 5.0 to about pH 8. In various aspects, the compositions comprise a therapeutically effective amount of at least one compound as described herein, together with one or more pharmaceutically acceptable excipients. Optionally, the compositions comprises a combination of the compounds described herein, or may include a second active ingredient useful in the treatment or prevention of bacterial growth (for example and without limitation, anti-bacterial or anti-microbial agents), or may include a combination of reagents of the invention.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol) wetting or emulsifying agents, pH buffering substances, and the like.

EXAMPLES

The invention will be more fully understood by reference to the following examples which detail exemplary embodiments of the invention.

Materials and Methods Used in the Examples

Materials

All chemicals and reagents were analytical grade and purchased from Sigma-Aldrich (St. Louis, Mo.) unless otherwise noted. Near infrared dyes, Cy5 and Cy5.5 were purchased from Lumiprobe (Hallandale Beach, Fla.). Peptide synthesis reagents were obtained from Anaspec (Anaspec, Fremont, Calif.) or AAPPTEC (AAPPTEC, Louisville, Ky.) and were of the highest grade available (>99% purity) and used without further purification. The claudin-1 (CLDN1) extracellular loop mimetic peptide (Cldn1 53-80 with biotinylated C-terminus) was purchased from Biomatik (Wilmington, Del.). Primary rabbit anti-claudin 1 polyclonal antibody (clone Jay.8) and primary mouse anti-β-tubulin monoclonal antibody (Clone 2-28-33) were both purchased from Invitrogen. Secondary antibodies, HRP-conjugated donkey anti-Rabbit IgG and HRP-conjugated sheep anti-mouse HRP were both purchased from GE Healthcare Life Sciences.

Cell Lines

Human colorectal adenocarcinoma cell lines (SW620, SW480, and HCT116) were obtained from the American Type Culture Collection (Manassas, Va.). Both SW620 and SW480 cell lines were cultured in Dulbecco's Modified Eagle Medium while the HCT116 cell line was cultured in McCoy's 5a Medium in a 37° C. humidified incubator with 5% $CO_2$. All cell culture medium was purchased from Gibco (Grand Island, N.Y.) and supplemented with 10% fetal bovine serum and 1% penicillin/streptomycin.

Identification of Cell Surface Target

A publicly available gene expression dataset (GEO series GSE41258) was utilized to identify cell membrane proteins that were upregulated in adenoma and adenocarcinoma tissue samples compared to normal tissue (Sheffer, 2009). In this database, 22,283 probe-sets had been analyzed using the Affymetrix HG_U133A array platform. The gene expression data from primary tumors, polyps, and normal colon samples were selected and transformed to base-2 logarithms. Two-sample T-tests and average fold-changes were computed between tumors and normal tissues and between polyps and normal tissues. Data was refined to 91 up probe-sets based on the following criteria: p-value less than 0.00001, average fold-change of greater than or equal to 2, and located at the plasma membrane.

Identification of Peptide Specific for CLDN1

Peptide specific for CLDN1 were identified through the phage display technique using the PhD7 phage library (New England Biolabs, Ipswich, Mass.) according to the manufacturer's guidelines. The panning process was performed on 15 mm dishes coated with 0.1 mg/mL streptavidin, washed with TBST (Tris buffered saline (TBS) with 0.1% Tween-20), and blocked for 1 h at 4° C. with blocking buffer (0.1 M $NaHCO_3$ with 0.5% bovine serum albumin (BSA) and 0.1 m/mL streptavidin). The phage library ($1 \times 10^{11}$ pfu containing $1.28 \times 10^9$ unique seven amino acid sequences) was first cleared for non-specific binding sequences by panning against two streptavidin-coated 15 mm dishes and one uncoated dish for 30 minutes at room temperature (RT) with agitation. Unbound phage was collected after each clearing step and used in subsequent clearing steps. After the third and final round of clearing, phage were amplified and titered. To perform the biopanning process against CLDN1, the biotinylated CLDN1 ECD peptide was pre-complexed with $2 \times 10^{11}$ cleared, amplified phage before adding to a blocked streptavidin-coated dish for 30 minutes at RT with agitation. After 30 minutes, biotin was added at a final concentration of 0.1 mM for 5 minutes to bind any free streptavidin. Dishes were washed 10 times with TBST and weak binders were removed by eluting with elution buffer (0.2 M glycine, pH 2.2, with 1 mg/mL BSA) for 2 minutes. A second elution was performed for 13 minutes to elute strong binders. Eluate containing the strong binders was neutralized with neutralization buffer (1M Tris-HCl, pH 9.1), amplified, and titered before performing the next round of biopanning. Three rounds of biopanning were performed with decreasing concentrations of biotinylated CLDN1 ECD (75 nM, 50 nM, and 25 nM, respectively) that were pre-complexed with $2 \times 10^{11}$ phage for decreasing periods (60, 40, and 20 minutes, respectively). Additionally, the concentration of Tween-20 in the washing buffer in rounds 2 and 3 was increased from 0.1% to 0.5%. The unamplified eluate from the strong binders of rounds 2 and 3 were titered overnight and 50 plaques selected for DNA sequencing (University of Michigan DNA Sequencing Core).

Synthesis of Peptide Specific for CLDN1

The phage peptide sequence that was highly enriched after three rounds of biopanning, RTSPSSR, was synthesized using standard solid phase Fmoc chemistry and labeled at the C-terminus with one of two fluorescent dyes, Cy5 or Cy5.5, via a 5 amino acid linker, GGGSK (SEQ ID NO: 24). A control scrambled sequence, SPTPSSR (SEQ ID NO: 25), was similarly synthesized and labeled with either dye via the same linker. Synthesis of both peptides was performed on a PS3 automatic synthesizer (Protein Technologies, Inc., Tucson, Ariz.) using Boc and Fmoc protected L-amino acids before manually labeling with the dye. Upon completion of peptide synthesis, the ivDde side chain was removed with 5% hydrazine in dimethylformamide (DMF) with agitation for 3×20 minute periods at RT. Unwanted Fmoc removal during this step was prevented by using a Boc-protected N-terminal amino acid and Fmoc-Lys (ivDde)-OH as the C-terminal amino acid. The resin-linked peptide was then washed three times with DMF and dichloromethane (DCM). The fluorophore (Cy5 or Cy5.5) was then added along with Di-isopropylethylamine and incubated for 24-48 h with agitation at RT. The peptide was then cleaved from the resin with ice-cold trifluoroacetic acid (TFA):triisopropylisilane:water (9.5:0.25:0.25, v/v/v) for 4 hours with agitation at RT. Peptide was separated from the resin and solvents evaporated with $N_2$ gas before precipitating the peptide with diethyl ether in an overnight incubation at −20° C. The precipitate was collected by centrifugation at 1780×g for 5 min and resuspended in acentonitrile:water (1:1, v/v). Both peptides were purified to >95% via HPLC (Waters, Milford, Mass.) using a water (0.1% TFA)-acetonitrile (0.1% TFA) gradient and produced an experimental mass-to-charge (m/z) ratio of 1639.91 and 1740.9 for Cy5-labeled and Cy5.5-labeled peptides, respectively, via mass spectrometry, in agreement with expected calculations.

Immunocytochemistry

SW620, SW480, and HCT116 cells were plated at density of 0.5×106 cells/mL in a 12-well plate. The following day, they were fixed with ice-cold methanol for 20 min at −20° C., blocked with PBS+2% BSA for 1 h at RT, then incubated first with primary antibody (anti-CLDN1 Ab at 5 μg/mL) at 4° C. overnight, then secondary antibody (goat anti-rabbit AF488, Life Technologies, 1:500) for 1 h at RT. Finally, cells were counterstained with DAPI+Prolong Gold before placing on slides and imaging with a Leica SP5× confocal microscope using a 63× (numerical aperture=1.4) oil-immersion objective.

Analysis of Cytoplasmic/Plasma Membrane Fractions for Presence of CLDN1

The cytoplasmic and plasma membrane fractions were extracted from SW620, SW480, and HCT116 cells using the BioVision Plasma Membrane Protein Extraction Kit according to the manufacturer's instructions. The total protein in the cytoplasmic and plasma membrane fractions were quantified using a BCA protein assay kit (Pierce) and 3 μg total protein of each fraction were run on a Novex 4-20% 1.5 mm protein gel before transferring to a PVDF membrane. The membrane was blocked with PBST+5% non-fat milk for 1 h at 4° C., stained with either rabbit anti-CLDN1 Ab or mouse anti-tubulin Ab at 4° C. overnight, then with anti-rabbit HRP (1:500, for CLDN1) or anti-mouse HRP (1:500, for tubulin) for 1 h at RT before developing.

siRNA Knockdown of CLDN1 Expression

CLDN1 expression was knocked down using Dharmacon On-Target Plus SMARTpool Human CLDN1 siRNA (Thermo Scientific) according to the manufacturer's protocol. SW620 cells were plated overnight on coverslips in a 12-well plate at 0.2×10⁶ cells/mL. The following day, cells were transfected with 3 μL DharmaFECT1 and either 25 nM CLDN1 or control siRNA. After 72 h, transfected cells were analyzed for CLDN1 expression through immunocytochemistry, a peptide binding study, or a Western blot of the cell lysate. For the immunocytochemistry experiment, cells were fixed with ice-cold methanol for 20 minutes at −20° C., blocked for 1 h at RT with PBS+2% BSA, stained with anti-human CLDN1 antibody at 5 μg/mL for 1 h at RT, then with goat anti-Rabbit AF488 (1:500) for 1 h at RT before being mounted on slides with DAPI with Prolong Gold. siRNA-transfected cells were also stained with 5 μM RTS-Cy5.5 or SPT-Cy5.5 for 30 minutes at 4° C., fixed with 4% PFA for 10 minutes at RT, then mounted on slides. Simultaneously, transfected cells were lysed with RIPA buffer containing Roche Mini-Complete EDTA-free Protease Inhibitor for 10 minutes on ice, collected and spun at 20,000×g for 10 minutes at 4° C. Supernatant was saved, total protein concentration quantified via a BCA assay, and 10 ug protein of each sample run on a Novex 4-20% 1.5 mm protein gel before transferring to a PVDF membrane. The membrane was blocked with PBST+5% non-fat milk for 1 h at 4° C., stained with either rabbit anti-CLDN1 Ab or mouse anti-tubulin Ab at 4° C. overnight, then with anti-rabbit HRP (1:500, for CLDN1) or anti-mouse HRP (1:500, for tubulin) for 1 h at RT before developing.

Competitive Binding Assay

SW620 cells were plated at 0.5×10⁶ cells/mL on coverslips on 12-well plates. The following day, the cells were treated first with unlabeled RTS* peptide at 0, 25, 50, 100, 200, or 400 μM for 30 min at 4° C., washed with PBS, and then treated with 5 μM of RTS*-Cy5.5 for 30 min at 4° C. The cells were fixed with 4% PFA for 5 min at RT, washed, and counterstained with DAPI with Prolong Gold while placing on slides. Fluorescent images were collected with a Leica SP5× confocal microscope using a 63× (numerical aperture=1.4) oil-immersion objective. Fluorescence intensities were quantified via Matlab Software.

Cell Binding Assay

SW620, SW480, and HT29 cells were plated at 0.5×10⁶ cells/mL on coverslips on 12-well plates. The following day, the cells were treated with either 10 μM either RTS*-Cy5.5 or SPT*-Cy5.5 for 1 h at 4° C., fixed with 4% PFA for 10 minutes at RT, then counterstained with DAPI with Prolong Gold. Fluorescent images were collected and analyzed as detailed above. Statistical analysis was performed using a one-way ANOVA analysis on GraphPad Prism.

Characterization of Peptide Binding

The apparent dissociation constant of RTS*-Cy5.5 to SW620 cells was measured. SW620 cells were washed two times with PBS+0.5% BSA, then 1×10⁵ cells were incubated with RTS*Cy5.5 at dilutions ranging from 0-200 nM for 1 h at 4° C. Cells were then washed of unbound peptide 5 times with PBS+0.5% BSA before analyzing via flow cytometry (FACS Canto, BD). Sample means were used to calculate the equilibrium dissociation constant, $k_d$, via non-linear regression analysis using GraphPad Prism software.

To measure the apparent association time constant of RTS*-Cy5.5, SW620 cells were washed two times with PBS+0.5% BSA, then 1×10⁵ cells were incubated with 5 μM RTS*Cy5.5 at 4° C. for different time intervals ranging from 2-15 min. The cells were immediately washed of unbound peptide several times with PBS+0.5% before analyzing via flow cytometry. The mean fluorescent intensity of SW620 cells at the various time points was ratioed with that of untreated cells and used to calculate the rate constant, k, by fitting the data to a first order kinetics model, $y(t)=I_{max}[1-\exp^{(-kt)}]$, using Origin 6.1 software.

In Vivo Imaging

A genetically engineered mouse model (Cpc;Apc) that spontaneously forms adenomatous polyps in the colon was used for this study and handled according to Institutional Guidelines. The colons of anesthetized mice were first cleaned with water before imaging with a small animal endoscope (Karl Storz Veterinary Endoscope) using the white light channel to locate polyps by identifying anatomic landmarks and the distance of the endoscope tip from the anus. A 100 µM solution of either RTS*-Cy5.5 or SPT*-Cy5.5 was applied topically and allowed to incubate for 5 minutes before rinsing thoroughly with water to remove unbound peptide. Fluorescent and reflectance images were then collected with the same endoscope set to the appropriate channels. Once in vivo imaging was complete, four of the mice used in the study were euthanized and colons harvested. Polyps and flat lesions detected during fluorescence imaging were located, removed, and processed for histology (H&E).

Ex Vivo Tissue Staining

Human colon tissue was obtained through consenting patents at the University of Michigan Hospital. Tissue was frozen in OCT and sectioned 10 µm thick using a Cryostat. The sections were thawed before staining with 10 µM RTS*-Cy5 for 15 minutes at RT. Tissues were then washed with PBS, fixed with 4% PFA for 10 min at RT, and counterstained with DAPI with Prolong Gold. Fluorescence was imaged and quantified as outlined above.

Validation of Claudin-1 Expression in Mouse and Human Specimens

Formalin-fixed sections from mouse and human proximal colon were deparaffinized. Antigen retrieval was performed using standard methods. Briefly, the sections were incubated 3 times in xylene for 3 min, washed 2 times with 100% ethanol for 2 min, and washed 2 times with 95% ethanol for 2 min. Rehydration was performed by washing in dH2O for 5 min. Antigen unmasking was performed by boiling the slides in 10 mM sodium citrate buffer with 0.05% Tween at pH 6.0, and then maintaining at a sub-boiling temp for 15 min. The slides were cooled for 30 min. The sections were washed 3 times in dH2O for 3 min, and then incubated in 3% H2O2 in methanol for 10 min. The sections were washed 3 times in dH2O for 2 min and in PBST for 5 min. For the mouse specimens, we used 1:200 dilution of polyclonal goat anti-claudin-1 (Abcam). For the human specimens, we used primary anti-claudin-1 antibody (Invitrogen clone Jay.8) that cross-reacts with human tissues at a concentration of 1:200 dilution. Blocking was performed with protein blocking agent (DAKO, X0909) for 15 min at RT. The blocking solution was washed off 3 times with PBS. The sections were incubated overnight at 4° C. in a humidified chamber and then washed 3 times in PBST for 5 min. A 1:200 dilution of biotinylated secondary antibody (goat anti-rabbit IgG) was added to each section and incubated for 30 min at RT. The secondary antibody solution was removed by washing 3 times with PBST for 5 min. Pre-mixed Elite Vectastain ABC reagent (Vector Labs) was added to each section and incubated for 30 min at RT. The sections were washed 3 times in PBS for 5 min, and developed with DAB substrate. The reaction was monitored for up to 5 min, and then quenched by immersing the slides in dH2O. Hematoxylin was added as a counterstain for ~20 sec, and the sections were dehydrated in increasing concentrations of ethyl alcohol (2 times at 70%, 80%, and 95% followed by 2 times at 100%). Coverslips were mounted using permount mounting medium (Fisher, # SP15-100) in xylene. Serial sections were processed for routine histology (H&E).

Immunofluorescence of Proximal Human Colon with Claudin-1 Peptide and Antibody

Formalin-fixed, paraffin-embedded (FFPE) specimens from human proximal colon were obtained from the archived tissue bank in the Department of Pathology at the University of Michigan. 5 µm thick sections were cut, mounted onto glass slides (Superfrost Plus, Fischer Scientific). The tissues were deparaffinized using a standard protocol. The sections were incubated with 3 rounds of xylene (3 min each) and 2 rounds of 100% and 95% ethanol (2 min each), and hydrated with water for 5 min. Antigen retrieval was performed with 10 mM citric acid buffer containing 0.05% Tween 20; pH 6.0. The specimens were placed in a citric acid buffer, maintained at a sub-boiling temperature for 15 min, and then allowed to cool to RT for 30 min. The sections were blocked with protein serum from DAKO for 15 min at RT followed by rinsing with PBS. The sections were then stained with RTS*-Cy5.5 at 5 µM concentration for 10 min at RT. The sections were then washed 3 times with PBS (3 min each) and incubated overnight with 1:200 dilution of primary anti-claudin-1 antibody (Invitrogen clone Jay.8). The sections were washed 3 times with PBST, and incubated with a 1:500 dilution of Alexa Fluor 488-labeled secondary goat anti-rabbit antibody (Invitrogen) for 1 hour at RT. The sections were washed again 3 times with PBST and mounted with Prolong Gold reagent containing DAPI (Invitrogen) using #1 cover glass (1.5 µm thickness). Confocal fluorescence images were collected with using a 63× oil immersion objective (Leica TCS SP5 Microsystems). The images were collected with the same exposure time for all specimens, including adenomas, sessile serrated adenomas, hyperplastic polyps and normal colonic mucosa.

The mean fluorescence intensities from 3 boxes with dimensions of 20×20 µm2 placed completely within the surface epithelium of each image was measured for RTS*-Cy5.5 using custom Matlab software (MathWorks Inc). Regions that showed intensity saturation were avoided. The results were transformed in base 2 log to improve normality and stabilize variance, and then fit with a one-way ANOVA model. Adjacent sections were processed for routine histology (H&E), and reviewed by 2 gastrointestinal pathologists (SRO and HDA). The peptide stained images were also correlated with immunohistochemistry on serial sections, as mentioned above.

Transepithelial Electrical Resistance (TEER) Measurements

T84 human colon carcinoma cells were grown in a 1:1 mixture of DMEM and Ham's F-12 culture medium supplemented with 5% FBS. To establish polarized monolayer, the cells were plated on transwell permeable polyester supports (1.12 cm$^2$, pore size 3 µm, Costar) until they reached confluence after ~3-4 days, as determined by an increase in TEER.43 The cells were continually grown on transwell supports until the TEER reached ~2000 Ω-cm$^2$. Then, 5 µM of either RTS-Cy5.5 or control peptides were added. TEER was then measured at 6, 12 and 24 hours. The cells were fixed with 4% PFA for 12 min. After brief washing, 1% SDS in PBS was used to permeabilize the cells. These procedures were followed by 3% goat serum in PBS blocking for 30 min. Mouse anti-zonula occludens-1 (anti-ZO-1) (1:250, Life Technologies) and rabbit anti-claudin-1 (1:200, Life Technologies) antibodies were diluted in block buffer and incubated in humidity box overnight at 4° C. and fluorescent secondary antibodies were diluted to 1:1000 and incubated

Example 1

Expression of Claudin-1

We identified claudin-1 as a promising target for detecting colonic neoplasia using the GEO series GSE41258 gene expression dataset [Sheffer et al., *Proc. Natl. Acad. Sci USA*, 106: 7131-7136 (2009)]. In this database, 22,283 probe-sets were analyzed using the Affymetrix HG_U133A array platform. The gene expression data from normal colon, adenoma, and adenocarcinoma (ACA) were selected and transformed into base-2 log. Two-sample t-tests and average fold-changes were computed. The data was refined to 91 up probe-sets based on the following criteria: P-value <0.00001, average fold-change >2, and location on cell surface. A total of 1 normal and 3 ACA samples did not meet criteria from principal component analysis and were removed, resulting in 52 normal, 45 adenomas, and 164 ACA for analysis. Claudin-1 (CLDN1, arrow) showed excellent separation in expression for normal colonic mucosa compared to adenoma and ACA, P-value <$8.5\times10^{-18}$ and <$2.9\times10^{-44}$, respectively, by two-sample t-test (FIG. 1A,B). Receiver operator characteristic (ROC) curves for these data demonstrate high detection sensitivity and specificity (arrows) for adenoma (94%, 91%) and ACA (96%, 95%) with area-under-the-curve (AUC) of 0.882 and 0.983, respectively (FIG. 1C,D).

Figure 11:
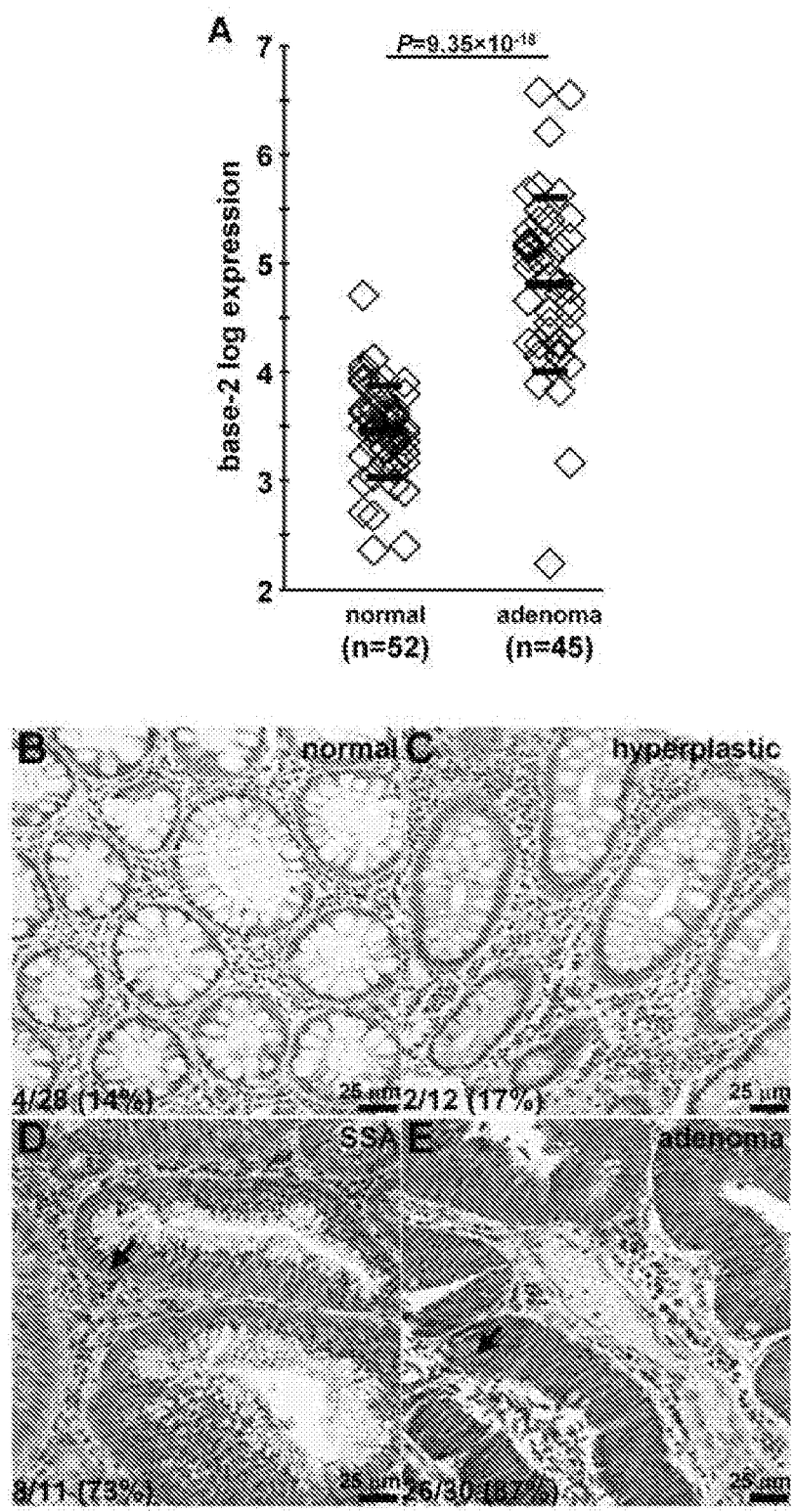
FIG. 11 shows the claudin-1 expression in proximal human colon. A) Claudin-1 (CLDN1) showed a 2.5-fold increase in gene expression between human adenomas (n=45) and normal (n=52) colonic mucosa from the GSE41258 dataset with P=9.35×10$^{-18}$ by two-sample t-test. On immunohistochemistry of archived human specimens from the proximal colon, no staining was observed from representative sections of B) normal and C) hyperplastic polyps, while intense cell surface staining (arrows) was seen from representative sections of D) sessile serrated adenoma (SSA) and E) adenomas. Using a standard IHC scoring system, overexpression (2/3+) of claudin-1 was found in 14% (4/28) normal, 17% (2/12) hyperplastic polyps, 73% (8/11) SSA, and 87% (26/30) adenoma.

FIG. 11A shows a 2.5 fold increase for adenomas (n=45) compared to normal (n=52) specimens of human colonic mucosa on gene expression using the GSE41258 dataset with P=$9.35\times10^{-18}$ by two-sample t-test. We then evaluated claudin-1 expression in archived human specimens from the proximal colon using immunohistochemistry to assess the potential of this cell surface target to be developed for imaging. FIG. 11B,C shows no staining for representative sections of normal and hyperplastic polyps, respectively. FIG. 11D,E shows intense cell surface staining (arrows) for representative sections of sessile serrated adenoma (SSA) and adenomas, respectively. Consensus between 2 GI pathologists (SRO, HDA) using a standard IHC scoring system found overexpression (2/3+) in 14% (4/28) normal, 17% (2/12) hyperplastic polyps, 73% (8/11) SSA, and 87% (26/30) adenoma. These results support that claudin-1 is a promising target for imaging of pre-malignant lesions (SSA and adenomas) in the proximal colon.

Figure 5:
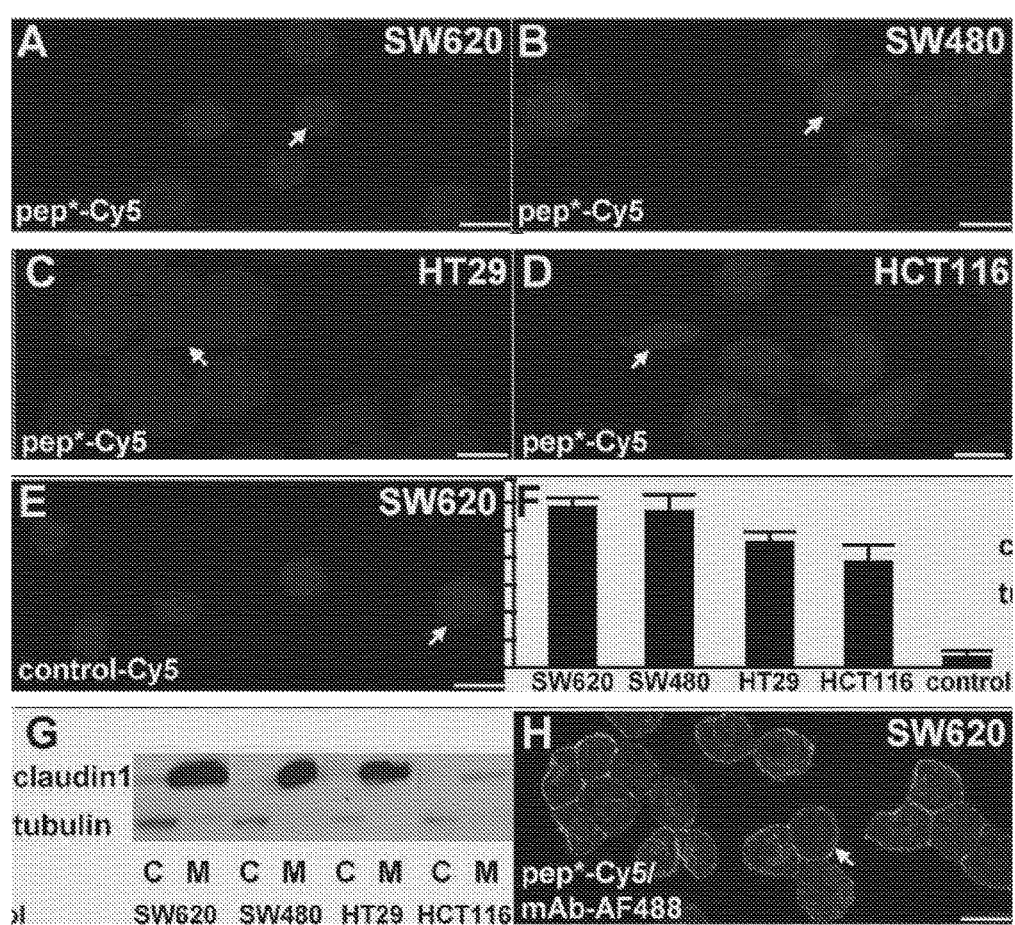
FIG. 5 shows reagent binding to a panel of human adenocarcinoma cells. Binding of pep*-Cy5 to human colon adenocarcinoma cells A) SW480, B) SW620, C) HCT116, and D) HT29. E) Cy5-labeled control peptide used with SW620. F) Quantified Cy5 fluorescence intensities. G) Western blot show claudin-1 expression levels in cytosol (C) and membrane (M). H) Co-localization of pep*-Cy5 (red) with anti-claudin-1-AF488 (green) binding to cells (arrow) shown on overlay image, correlation ρ=0.56, scale bar 10 μm.

We also verified that human colorectal adenocarcinoma cells SW620, SW480, and HT29 had high expression levels of claudin-1 (CLDN1) on the plasma membrane, thus making them good cell lines to validate candidate peptides. Isolation of the plasma membrane fraction (M) from the cytoplasmic fraction (C) of the adenocarcinoma cells verified not only that CLDN1 expression was elevated in plasma membrane versus cytoplasmic fractions of these cell lines, but more importantly, that it is expressed at a much higher level at the plasma membrane compared to the low-expressing cell line, HCT116. See FIG. 5G. With these results in mind, SW620, SW480 and HT29 cells were used as high CLDN1-expressing cell lines while HCT116 was used as a low CLDN1-expressing cell line in the experiments described below.

Example 2

Peptides Specific for Claudin-1

We used phage display technology to select candidate peptides that are specific for human claudin-1. We biopanned an M13 library against a 28-amino acid protein fragment of the extracellular domain of claudin-1 [Mrsny et al., supra]. Enrichment was found in twenty-three candidate phages after three rounds of biopanning. Peptides RTSPSSR (SEQ ID NO: 1), HLQLQRL (SEQ ID NO: 2), IQTNPTM (SEQ ID NO: 3), RSLTQQT (SEQ ID NO: 4), SLQHLRS (SEQ ID NO: 5), IQLKINS (SEQ ID NO: 6), ITIRQHI (SEQ ID NO: 7), RRSNSQL (SEQ ID NO: 8), LNRIRRR (SEQ ID NO: 9), NNMKKIT (SEQ ID NO: 10), LQSLISK (SEQ ID NO: 11), IHTRRRK (SEQ ID NO: 12), RPNKPRI (SEQ ID NO: 13), RHRRSPI (SEQ ID NO: 14), ITLSITQ (SEQ ID NO: 15), KTQLMII (SEQ ID NO: 16), RPRQLQR (SEQ ID NO: 17), TRRHTII (SEQ ID NO: 18), RIIHKNM (SEQ ID NO: 19), LLTISPK (SEQ ID NO: 20), LLPMHMN (SEQ ID NO: 21), TSPMLSI (SEQ ID NO: 22), and LRNNIRH SEQ ID NO: 23) were identified.

The peptide RTSPSSR (SEQ ID NO: 1) (abbreviated pep* or RTS* herein) that showed the highest level of enrichment was synthesized (non-GMP) in our lab using standard solid phase Fmoc chemistry and labeled at the C-terminus with either Cy5, Cy5.5, 5-TAMRA, AF488 or FITC via a GGGSK (SEQ ID NO: 24) linker (FIG. 2A). 5-FITC is used herein as the initial fluorophore for in vivo verification of imaging in mouse colon. The other fluorophores will be used for imaging in other regions of the visible spectrum. These experiments support feasibility of performing multiplexed imaging.

Example 3 siRNA Knockdown of Claudin-1

Figure 2:
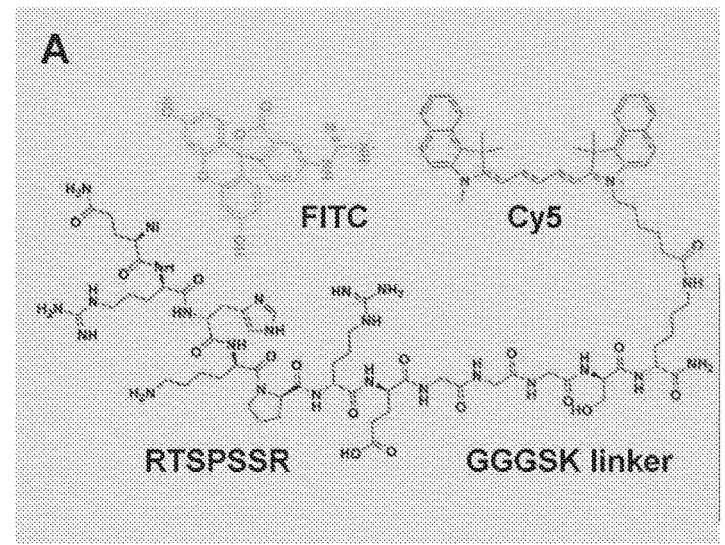
FIG. 2 shows an exemplary peptide reagent specific for claudin-1. A) Chemical structure of candidate peptide (pep*) specific for claudin-1 labeled with either Cy5 or FITC. B-G) Knockdown of claudin-1 (CLDN1) expression in cells with siRNA supports peptide specificity. H) Quantified results show significantly ↑ signal for siCL versus siCLDN1 cells (10.5 and 4.0 fold-change, P=0.001 and 0.002, respectively) with RTS*-Cy5.5 and anti-CLDN1 antibody, while SPT*-Cy5.5 showed a non-significant ↓ (0.80 fold-change, P=0.5). Differences for siCL versus siCLDN1 for RTS*-Cy5.5 and CLDN1 antibody were significantly greater than that for SPT*-Cy5.5 (P=0.005 and 0.008, respectively). We fit ANOVA models with terms for 3 treatments, 2 siRNA effects, and their interactions, for 3 replicate slides. I) Western blot show relative levels of claudin-1 expression in cells evaluated.
Figure 2:
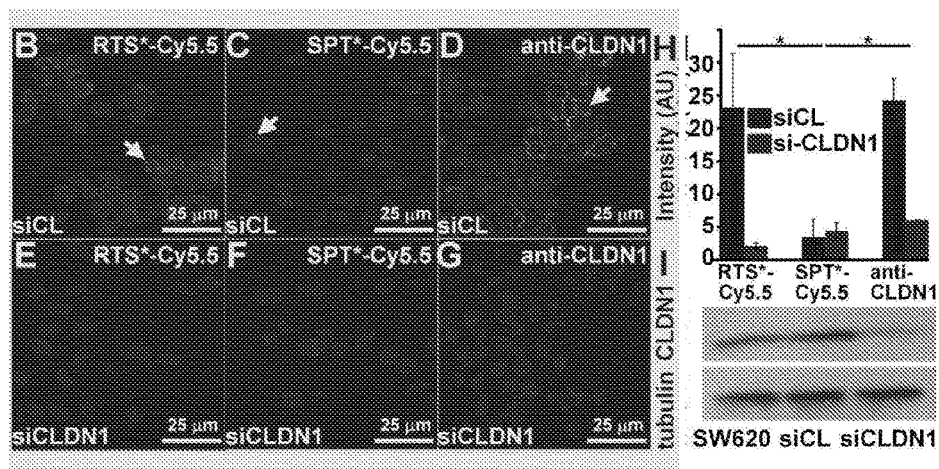

The specificity of peptide binding was validated on siRNA knockdown. RTS*-Cy5.5 reagent (red) and AF488-labeled anti-CLDN1 (green) show strong binding to the surface (arrows) of SW620 cells (FIG. 2B,D). These cells were transfected with siRNA to knockdown cell surface expression of claudin-1. The control peptide reagent SPT*-Cy5.5 shows minimal binding (FIG. 2C,F). A >4-fold reduction in fluorescence intensity was observed for binding to SW620 cells transfected with siRNA (siCLND1) for both the peptide reagent and antibody (FIG. 2E,G). Differences for siCL versus siCLND1 for RTS* and anti-CLND1 were significantly greater than that for SPT* (control). The fluorescence intensities (mean±std) are shown (FIG. 2H). A Western blot shows CLDN1 expression levels in SW620 cells (FIG. 2I). Given the experimental design and mean-squared-errors shown in FIG. 2H, with triplicate slides we have 98% power to obtain P<0.01 for interactions that show a 3-fold difference of differences.

Example 4

Competition for Peptide Binding

Figure 3:
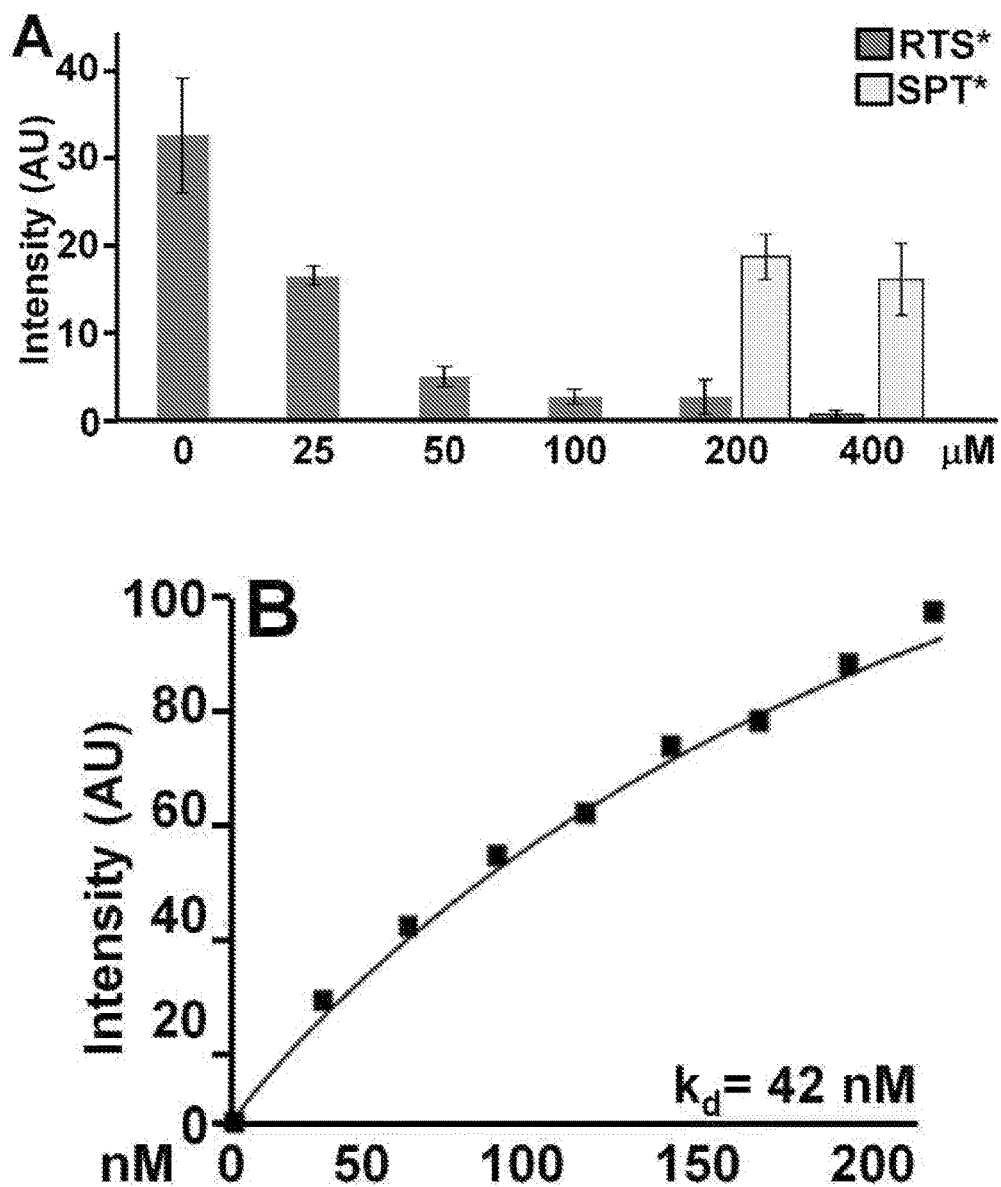
FIG. 3 shows the results of peptide reagent competition assays A) On competition, we found significant difference in binding of RTS*-Cy5.5 to SW620 cells that overexpress claudin-1 with addition of unlabeled RTS* and SPT*. B) The apparent dissociation constant (binding affinity) for RTS*-Cy5.5 to SW620 cells is $k_d$=42 nM, $R^2$=0.95. Results are representative of six independent experiments.

The specificity of peptide binding was also validated by competition assay. Cells were grown on cover glass and incubated first with unlabeled peptides with concentrations ranging from 0-400 μM, and then with the optimized peptide. The fluorescence intensities were measured with confocal microscopy. As an example, we evaluated binding of RTS*-Cy5.5 to SW620 cells on competition with addition of unlabeled RTS* and SPT* (control). We fit two-way ANOVA models with terms for the labeled peptide, concentrations of the unlabeled peptides and their interactions on log-transformed data. Significant differences were observed at concentrations of 25 μM and higher (FIG. 3A). With this study design, analysis and effect sizes, as shown in FIG. 3A using triplicate slides, we have 100% power to obtain P<0.01 for differences between 0 and 400 nM for differences between RTS* and SPT*.

Example 5

Characterization of Peptide Binding Affinity

The apparent dissociation constant ($k_d$) of the peptides to cells in vitro was determined. The fluorescently-labeled peptide was be serially diluted in PBS at concentrations that ranged from 0 to 200 nM in 25 nM increments. Cells were incubated with the peptide, and the mean fluorescence intensities was measured on flow cytometry. The equilibrium dissociation constant $k_d=1/k_a$ was calculated by performing a least squares fit of the data to the non-linear equation $I=(I_0+I_{max}k_a[X])/(I_0+k_a[X])$. $I_0$ and $I_{max}$ are the initial and maximum fluorescence intensities, corresponding to no peptide and at saturation, respectively, and [X] represents the concentration of the bound peptide [62]. This approach is illustrated with RTS*-Cy5.5 in FIG. 3B, where $k_d=42$ nM.

To measure the apparent association time constant of RTS*-Cy5.5, SW620 cells were washed 2× with PBS+0.5% BSA, then ~$10^5$ cells were incubated with 5 μM RTS*-Cy5.5 at 4° C. for time intervals ranging from 2-15 min. The cells were immediately washed of unbound peptide 5× with PBS+0.5% BSA before analyzing with flow cytometry. The mean fluorescence intensity of SW620 cells at the various time points was ratioed with that of untreated cells and used to calculate the rate constant k by fitting the data to a first order kinetics model, $y(t)=I_{max}[1-\exp^{(-kt)}]$, using Origin 6.1 software. An apparent association time constant k=0.83 $\text{min}^{-1}$ which corresponds to <1.2 min was measured.

Example 6

Peptide Binding to Adenocarcinoma Cells Using Peptide Labeled with Cy5 or FITC

Figure 4:
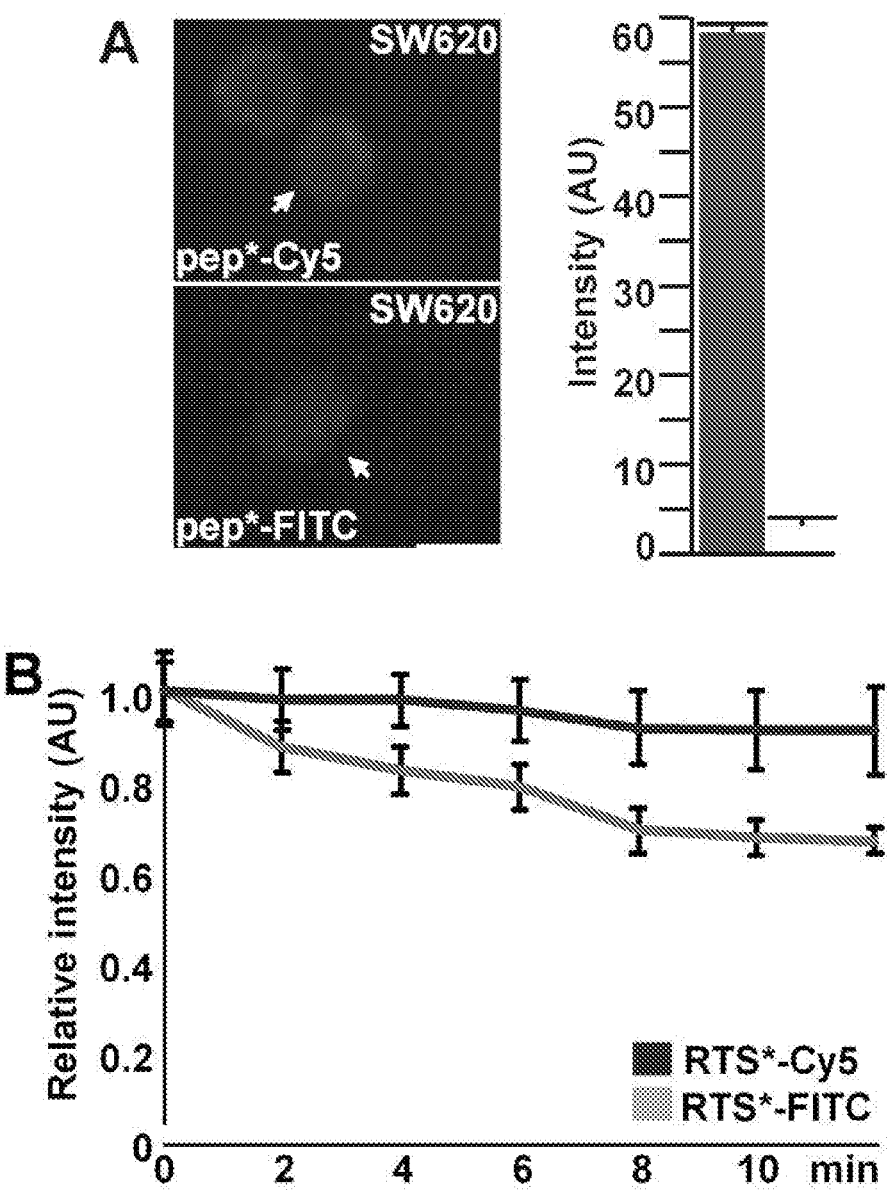
FIG. 4 shows a comparison between peptide labeled with FITC or Cy5 to human adenocarcinoma cells. A) Confocal images of peptide reagent binding to human SW620 colon adenocarcinoma cells (arrows) shows ~20-fold greater signal using the Cy5 label, scale bar 10 μm. B) Cy5-labeled peptide reagent shows ~4-fold improvement in photostability compared to FITC-labeled peptide at 12 min of continuous excitation.

We incubated pep*-Cy5 (RTS*-Cy5) and pep*-FITC (RTS*-Cy5) (10 μM) (FIG. 4A) with human colon adenocarcinoma (SW620) cells that over-express Claudin-1 at 4° C. for 1 hour. A supercontinuum "white light" laser provided continuous excitation at 1.5 mW for both $\lambda_{ex}$=647 and 488 nm. Confocal images (Leica TCS SP5 Microsystems) were collected using Cy5 and FITC filters every 2 min. At time 0 min, peptide (RTS*-Cy5) binding to the cell surface (arrow) is shown, scale bar 10 μm (FIG. 4B). The mean (±std) fluorescence intensities for the Cy5 and FITC-labeled peptides, measured from n=6 cells, were 58.4±3.7 and 3.1±0.6 A.U. respectively, resulting in ~20-fold increase in signal using the NIR fluorophore. We also found a 8.5% reduction in fluorescence intensity for pep*-Cy5 in comparison to 32% for pep*-FITC at 12 min, resulting ~4-fold improvement in photostability (FIG. 4C).

Next, we observed specific binding of the Cy5-labeled candidate peptide to the cell surface (arrow) of a panel of human colonic adenocarcinoma cells (SW620, SW480, HT29, and HCT116) that over-express claudin-1 (FIG. 5A-D, scale bar 10 μm). A Cy5-labeled control (unrelated) peptide showed minimal binding to SW620 cells. The cells were incubated with the peptide (10 μM) at 4° C. for 1 hour, washed 3× with PBS, fixed with 4% PFA, and mounted with ProLong Gold containing DAPI (Invitrogen). The mean (±std) fluorescence intensities were quantified using custom Matlab software (FIG. 5F). Levels of claudin-1 expression from cytosol (C) and membrane (M) of cells are shown on western blot (FIG. 5G). The cells were then incubated with 1:50 dilution of primary anti-claudin-1 rabbit mAb (4267, Invitrogen) for 1 hour at 4° C., and washed 3× with PBS at RT. The cells were further incubated with 1:500 dilution of rabbit secondary anti-mouse antibody labeled with Alexa Fluor 488 (Invitrogen) for 1 hour at RT. Co-localization of peptide (red) and antibody (green) binding to SW620 cells can be appreciated on the overlay fluorescence image (FIG. 5H). A Pearson's correlation of ρ=0.56 was calculated using custom Matlab software.

Example 7

Binding of Claudin-1 Peptide and Antibody to Human Colonic Tissue Ex Vivo

Figure 6:
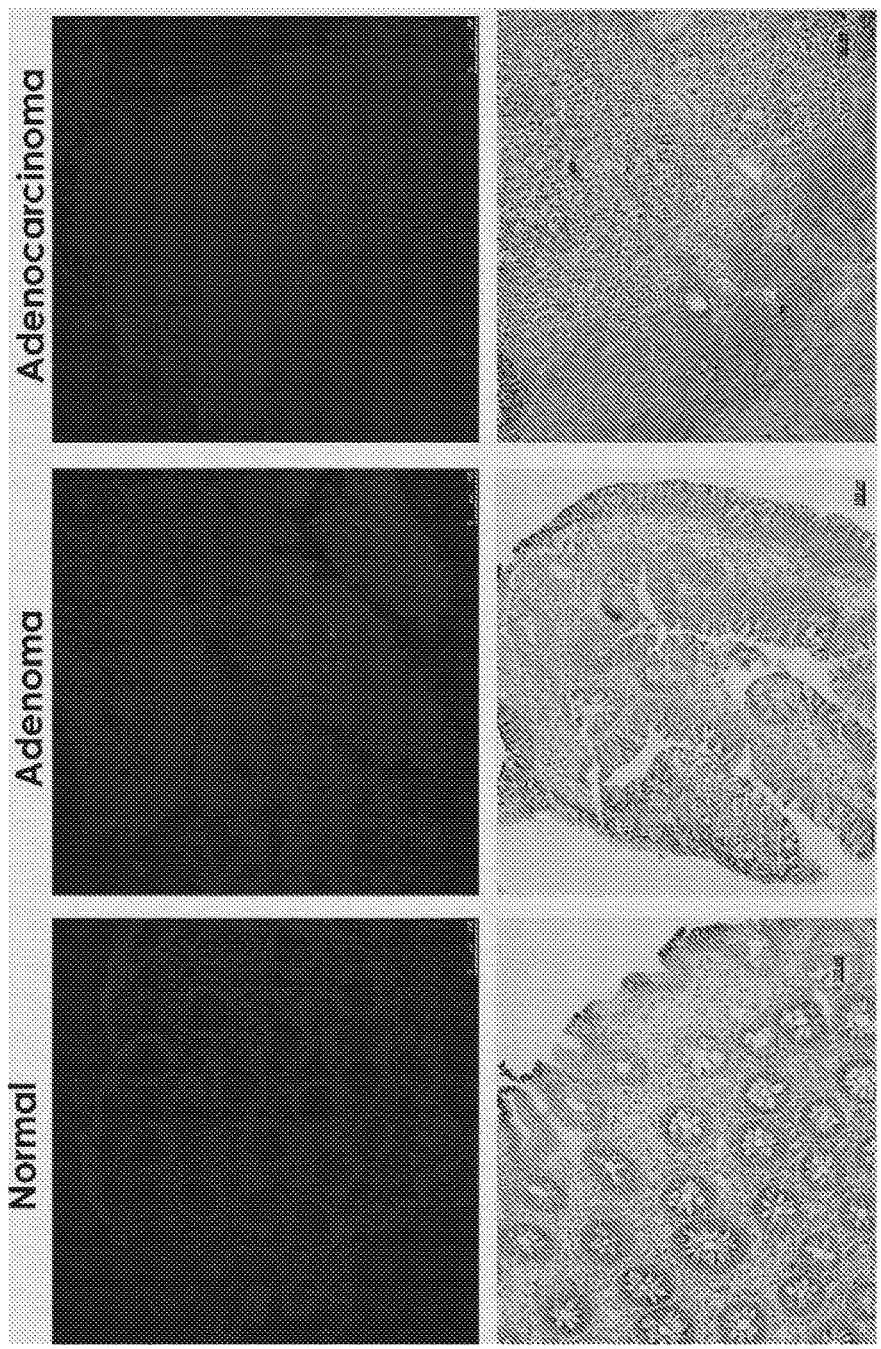
FIG. 6 shows the co-localization of peptide and anti-claudin-1 antibody binding to human colonic tissues. Binding to normal colonic mucosa, adenoma, and adenocarcinoma for pep*-Cy5 (red).

We have observed specific binding of the Cy5-labeled candidate peptide to human colonic tissues ex vivo (FIG. 6). Specimens of normal colonic mucosa, adenoma, and adenocarcinoma from the right side (proximal) of the colon were obtained from routine surveillance colonoscopy and surgically removed by endoscopic mucosal resection. The tissues were frozen in OCT (Sakura Finetek), cut in 10 μm sections, and incubated with pep*-Cy5 (5 μM) in 1×PBS for 15 minutes at RT. The sections were washed 3× with PBS. Confocal fluorescence images were collected from these sections with DAPI, FITC and Cy5 filter sets (Leica TCS SP5 Microsystems).

The mean fluorescence intensities (±SEM) from binding of pep*-Cy5 were measured for normal colonic mucosa (n=4, 7±2 AU), adenoma (n=6, 26±4 AU) and adenocarcinoma (n=5, 31±4 AU), P<0.001, unpaired t-test (FIG. 6, scale bar 500 μm). These images resulted in a T/B ratio of 3.7 and 4.4 for adenoma and adenocarcinoma, respectively, relative to normal. We found pep*-Cy5 and anti-claudin-1 mAb to stain colonic adenomas and adenocarcinomas in 11/12 (92%) and 10/10 (100%) sections, respectively.

Example 8

In Vivo Imaging of Colon in CPC;Apc Mouse

Figure 7:
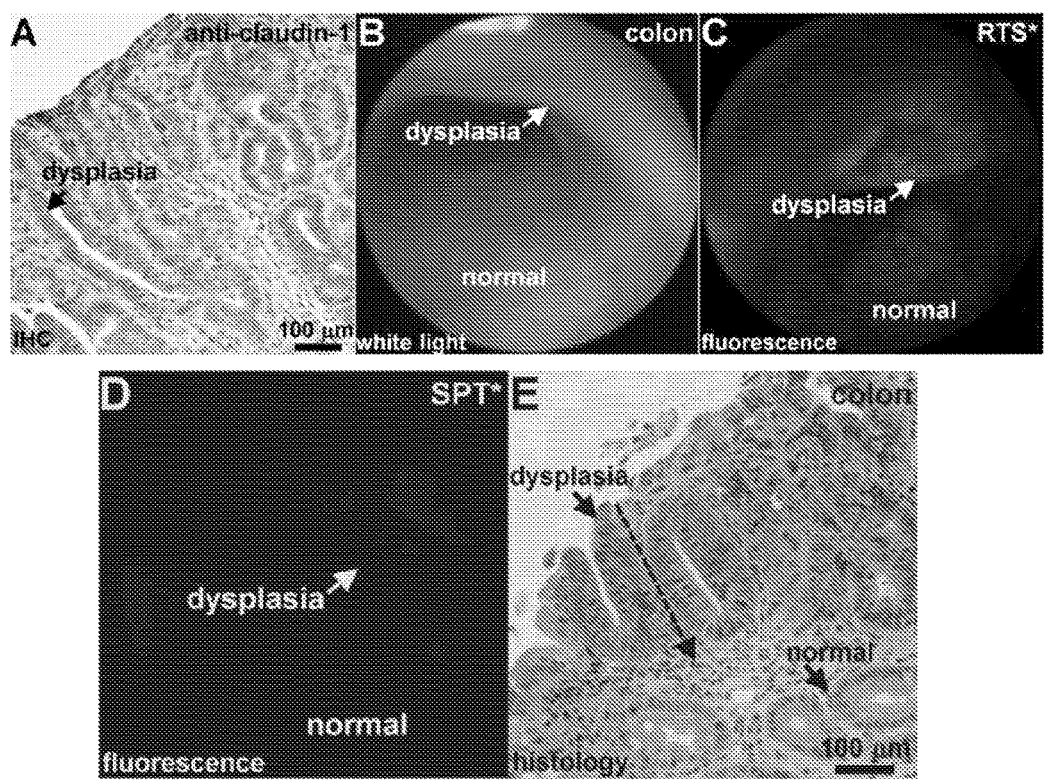
FIG. 7 shows the expression of claudin-1 in mouse colon. A) Expression of Claudin-1 in mouse colonic dysplasia (arrow) is validated on IHC using established antibody. B) White light endoscopy is performed in vivo in mouse colon to identify regions of dysplasia. C) After administration of RTS*-Cy5.5 reagent, increased fluorescence is seen from dysplasia (arrow) with high contrast and from some regions of normal mucosa. The T/B ratios (mean±SD) for RTS* and SPT* are 1.93±0.46 and 1.19±0.23, respectively, for n=10 dysplasias (1.95 fold change), P=6.4×10$^{-6}$ on paired, two-sided t-test. D) Fluorescence image with scrambled control peptide shows minimal signal, supporting specific binding of RTS* reagent. E) On histology, the depth (arrow) of dysplasia invasion into the epithelium can be measured.

Colonic dysplasia was detected on wide-field endoscopy in the colon of CPC;Apc mice. These mice are genetically-engineered to spontaneously develop colonic dysplasia [64], and the colonic lesions that develop are molecularly and histologically similar to that seen in human disease, making these mice a good model for monitoring cancer development. Because the extra-cellular domain of claudin-1 is completely homologous between human and mouse [4], peptides developed for human targets can be directly used in mouse imaging experiments. On immunohistochemistry (IHC), we used primary rabbit anti-claudin-1 antibody (clone Jay.8, Invitrogen), and found increased staining of this established antibody to claudin-1 on mouse colonic dysplasia (arrow), FIG. 7A. CPC;Apc mice were imaged at ~3 months of age when they first begin to develop dysplasia. An example of flat dysplasia (arrow) on white light is shown is shown in FIG. 7B. After administration of RTS*-Cy5.5, fluorescence images were collected. Increased signal is seen from dysplasia (arrow) and normal colonic mucosa (FIG. 7C). The control peptide reagent (SPT*) shows minimal signal, supporting specific binding by the RTS* peptide reagent to claudin-1 (FIG. 7D). After imaging is completed, mice were euthanized, and the colons were resected. Based on the location of dysplastic lesions determined using fluorescence images collected with endoscopy, a pathologist measured the depth of dysplasia on histology, as shown by the dashed arrow in FIG. 7E. As a demonstration of use in longitudinal studies, the final phase of in vivo testing is obtaining a sequence of images from the same mouse at multiple time points. Images are obtained from mice over at least three sessions separated by 1 week to monitor for cancer progression.

Figure 8:
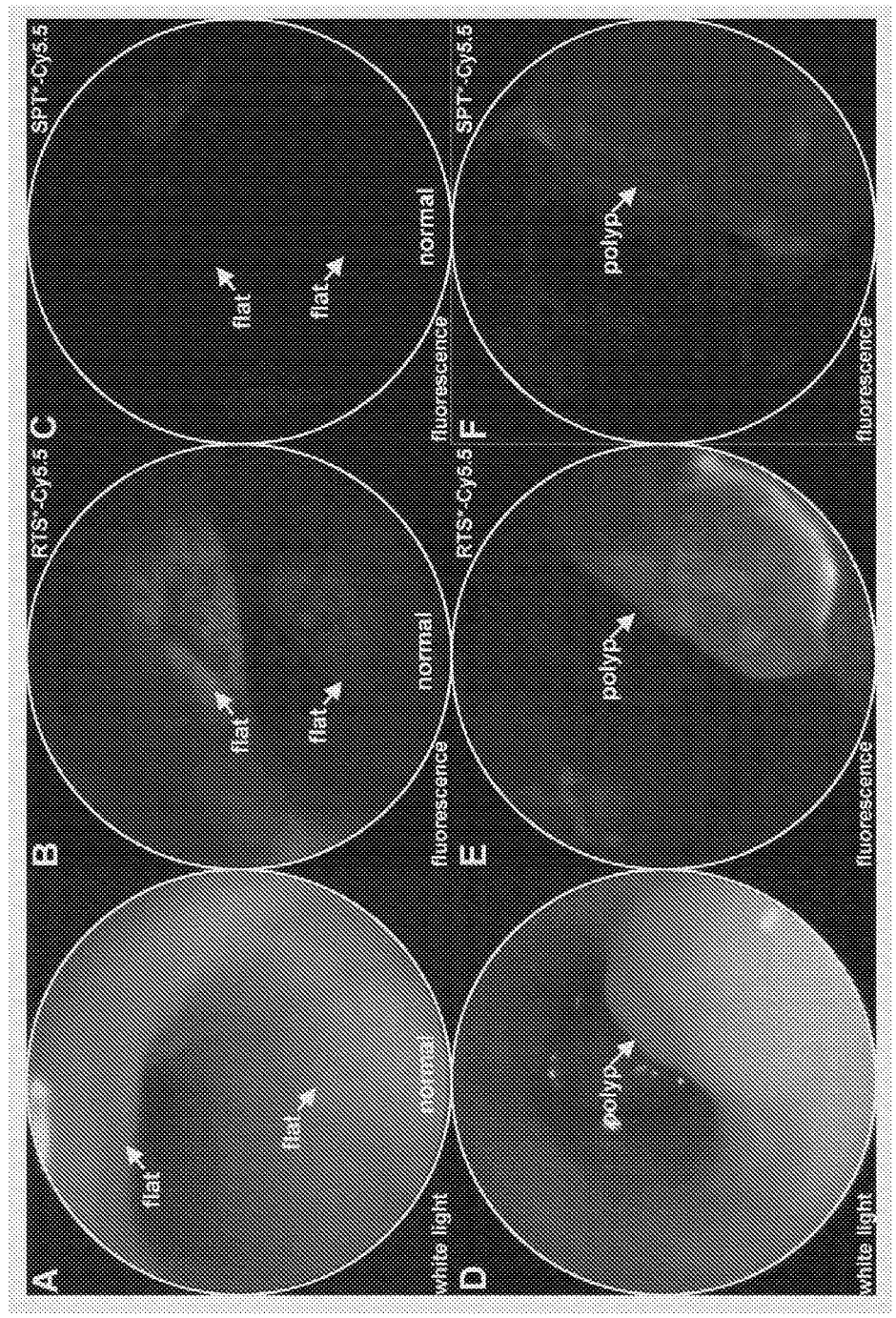
FIG. 8 shows fluorescent and reflectance images of polyps and flat lesions detected using RTS* and SPT* reagents in colon of a genetically engineered mouse model (Cpc:Apc).
Figure 9:
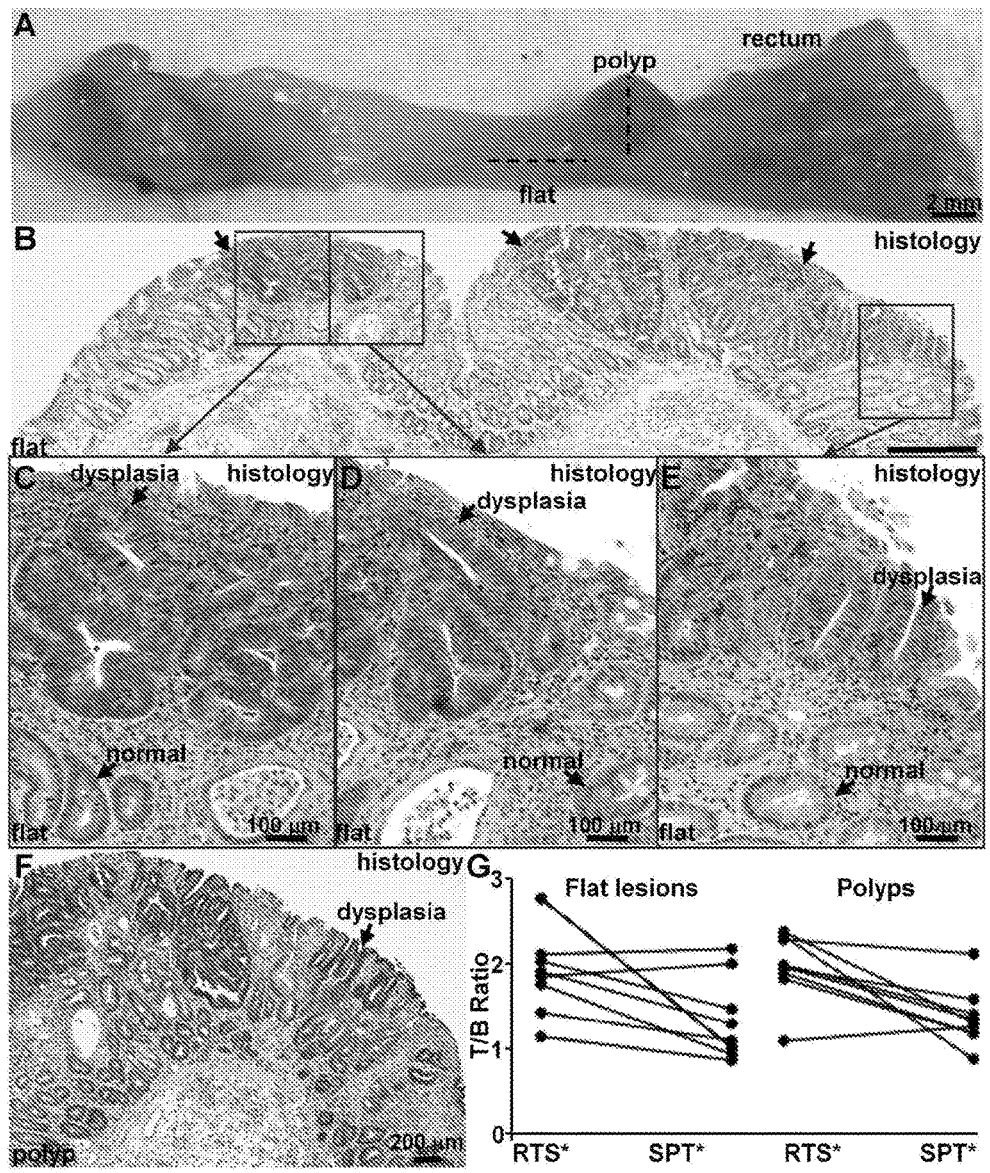
FIG. 9 shows polyps and flat lesions detected in the mouse model and processed for histology (H&E).

Additional images from fluorescence experiments are shown in FIG. 8 and from histology are shown in FIG. 9.

Example 9

Binding of Claudin-1 Peptide and Antibody to Proximal Human Colon

Figure 10:
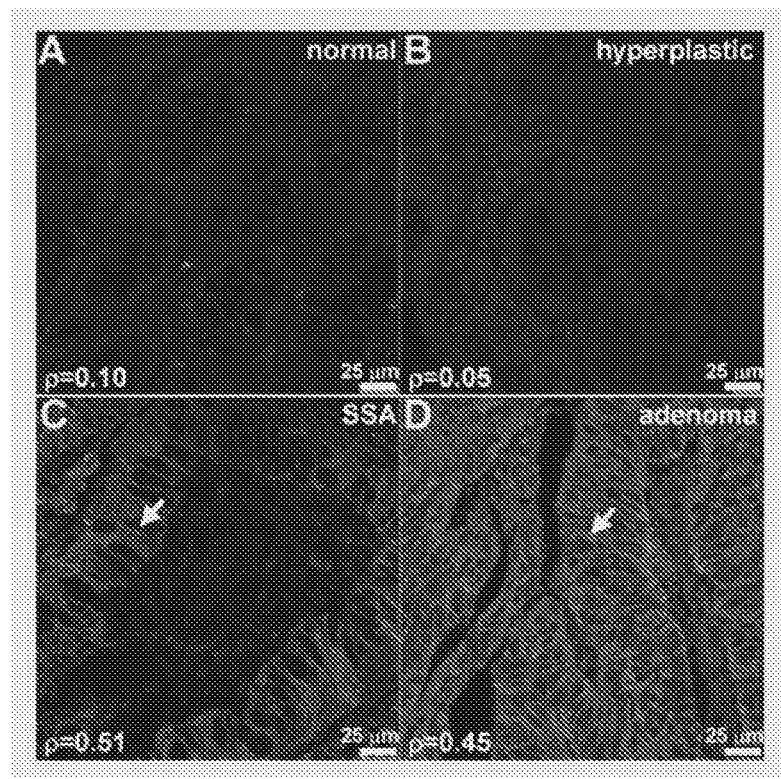
FIG. 10 shows the binding of RTS*-Cy5.5 reagent and antibody to proximal human colon. On confocal microscopy, there was minimal binding of RTS*-Cy5.5 reagent (red) and AF488-labeled anti-claudin-1 antibody (green) to human A) normal colonic mucosa and B) hyperplastic polyps. Strong staining with both peptide and antibody was observed for representative specimens of C) sessile serrated adenomas (SSA) and D) adenomas from the proximal colon. The fluorescence intensities from 3 boxes (20×20 μm$^2$) located randomly on cells within each specimen were measured and averaged. We found significantly greater intensities for adenomas versus normal and hyperplastic polyps (P=10$^{-5}$ and 8×10$^{-12}$, respectively), as well as for SSA versus normal and hyperplastic polyps (P=0.02 and 3×10$^{-7}$, respectively). Analysis used an ANOVA models with means for 4 groups, fit to log-transformed data.
Figure 10:
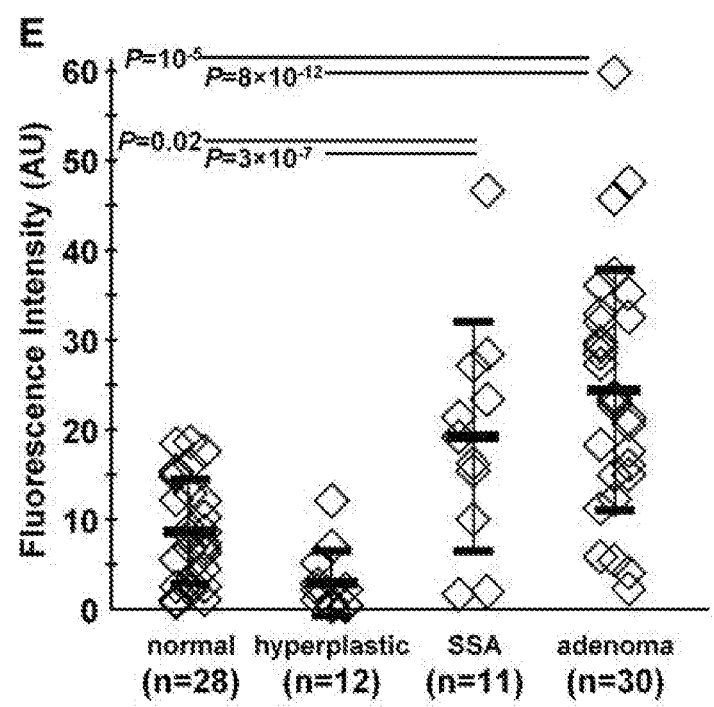

On confocal microscopy, FIG. 10A,B shows minimal fluorescence intensity to representative specimens of human normal and hyperplastic polyps, respectively, and FIG. 10C,D shows strong binding of the RTS*-Cy5.5 (red) and AF488-labeled anti-claudin-1 antibody (green) to the cell surface (arrows) in representative specimens of sessile serrated adenomas (SSA) and adenomas, respectively. Co-localization of peptide and antibody binding can be appreciated on these merged images, and the extent is characterized by the Pearson's correlation coefficient ρ. We measured the fluorescence intensities from binding of the RTS*-Cy5.5 peptide in a set of 3 boxes with dimensions of 20×20 μm² located at random on cells in the epithelium. We found a significantly greater mean±std result for adenomas versus normal and hyperplastic polyps and for SSA versus normal and hyperplastic polyps. FIG. 10E shows a mean fold-difference of 2.8 and 2.2 for adenoma and SSA versus normal, respectively.

Thus, the RTS*-Cy5.5 reagent was found to bind to human spontaneous sessile serrated adenomas and adenomas from the proximal human colon.

Example 10

Transepithelial Electrical Resistance (TEER) Measurements

Figure 12:
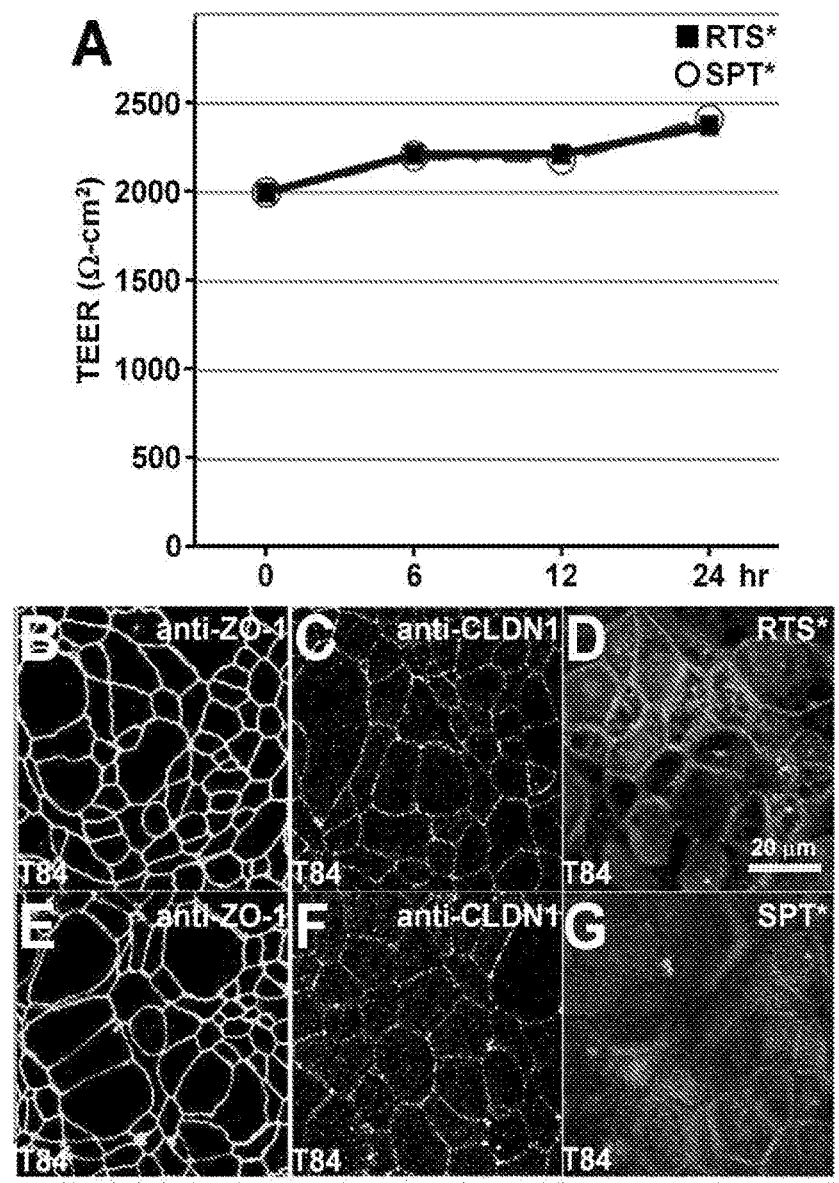
FIG. 12 shows that tight junction function and ZO-1 distribution are not altered by claudin-1 peptide. A) Confluent T84 monolayers were incubated with either 5 μmol RTS* or SPT* (control) peptides show high trans-epithelial electrical resistance (TEER) for up to 24 hours. Immunofluorescence demonstrates localization of B,E) anti-zonula occludens-1 (anti-ZO-1) and C,F) anti-claudin-1 (anti-CLDN1) antibodies on the apical plasma membrane of tight junctions at 24 hours after peptide incubation. D) RTS* peptide partially localizes to cellular junctions.

We evaluated the effect of peptide binding on tight junction function using a polarized monolayer of T84 cells plated on transwell supports. We found high trans-epithelial electrical resistance (TEER) with either RTS* or SPT* for up to 24 hours, FIG. 12A. On immunofluorescence, we observed antibodies for zonula occludens-1 (ZO-1), FIG. 12B,E, and claudin-1, FIG. 12C,F, to localize to the cell junctions. These results show that neither peptide alters tight junction function or ZO-1 distribution. The RTS* peptide localizes partially to cellular junctions by comparison to SPT*, FIG. 12D,G.

While the present invention has been described in terms of specific embodiments, it is understood that variations and modifications will occur to those skilled in the art. Accordingly, only such limitations as appear in the claims should be placed on the invention.

All documents cited in this application are hereby incorporated by reference in their entirety, with particular attention to the disclosure for which they are referred.

We claim:

1. A method for detecting colon dysplasia in a patient comprising the steps of administering a composition comprising a reagent to the colon of the patient and detecting binding of the reagent to dysplastic cells overexpressing claudin-1, wherein the reagent consists essentially of a peptide RTSPSSR (SEQ ID NO: 1) or a multimer form of the peptide, wherein the peptide specifically binds to claudin-1, and wherein at least one detectable label is attached to the peptide or a multimer form of the peptide.

2. A method for detecting colon pre-cancer, early colon cancer or colon cancer cells overexpressing claudin-1 in a patient comprising the steps of administering a composition comprising a reagent to the patient and detecting binding of the reagent, wherein the reagent consists essentially of a peptide RTSPSSR (SEQ ID NO: 1) or a multimer form of the peptide, wherein the peptide specifically binds to claudin-1, and wherein at least one detectable label is attached to the peptide or a multimer form of the peptide.

3. The method of claim 1 comprising at least one detectable label attached to the peptide.

4. The method of claim 3 wherein the detectable label is detectable by microscopy, photoacoustic, ultrasound or magnetic resonance imaging.

5. The method of claim 4 wherein the label detectable by microscopy is fluorescein isothiocyanate (FITC), Cy5, Cy5.5 or IRdye800.

6. The method of claim 3 wherein the detectable label is attached to the peptide by a peptide linker.

7. The method of claim 6 wherein a terminal amino acid of the peptide linker is lysine.

8. The method of claim 6 wherein the peptide linker comprises the sequence GGGSK set out in SEQ ID NO: 24.

9. The method of claim 1 wherein the multimer form of the peptide is a dimer formed with an aminohexanoic acid linker.

10. The method of claim 1, wherein the composition further comprises a pharmaceutically acceptable excipient.

* * * * *